US010582832B2

(12) United States Patent
Lawrence et al.

(10) Patent No.: US 10,582,832 B2
(45) Date of Patent: Mar. 10, 2020

(54) SYSTEM FOR ALTERING FUNCTIONS OF AT LEAST ONE SURGICAL DEVICE DEPENDENT UPON INFORMATION SAVED IN AN ENDOSCOPE RELATED TO THE ENDOSCOPE

(71) Applicant: Stryker Corporation, Kalamazoo, MI (US)

(72) Inventors: Hannah Lawrence, San Jose, CA (US); Benjamin Feingold, Tucson, AZ (US)

(73) Assignee: Stryker Corporation, Kalamazoo, MI (US)

( * ) Notice: Subject to any disclaimer, the term of this patent is extended or adjusted under 35 U.S.C. 154(b) by 377 days.

(21) Appl. No.: 15/467,055

(22) Filed: Mar. 23, 2017

(65) Prior Publication Data
US 2017/0188802 A1 Jul. 6, 2017

Related U.S. Application Data

(63) Continuation-in-part of application No. 14/155,480, filed on Jan. 15, 2014.
(Continued)

(51) Int. Cl.
*A61B 1/00* (2006.01)
*A61B 1/06* (2006.01)
(Continued)

(52) U.S. Cl.
CPC ...... *A61B 1/00006* (2013.01); *A61B 1/00016* (2013.01); *A61B 1/00029* (2013.01);
(Continued)

(58) Field of Classification Search
CPC ............ A61B 1/00006; A61B 1/00059; A61B 1/00101; A61B 1/0661; A61B 1/0669;
(Continued)

(56) References Cited

U.S. PATENT DOCUMENTS 4,279,246 A 7/1981 Chikama
4,697,894 A 10/1987 Takamura
(Continued)

FOREIGN PATENT DOCUMENTS

CN 102292014 A 12/2011
EP 3 263 014 A1 1/2018
(Continued)

OTHER PUBLICATIONS

Brochure by Stryker® ; "SafeLight™ Fiber Optic Cable"; known before invention (14 pages).
(Continued)

*Primary Examiner* — John P Leubecker
(74) *Attorney, Agent, or Firm* — Morrison & Foerster LLP

(57) ABSTRACT

An endoscopic system including an endoscope having saved information therein related to the endoscope, a light source console for providing light to the endoscope, and a light cable connected between the endoscope and the light source console. The light cable is configured to communicate the light from the light source console to the endoscope. The information related to the endoscope is relayed from the endoscope to the light source console through the light cable for altering functions of at least one of the light source console and an auxiliary device.

32 Claims, 18 Drawing Sheets

Related U.S. Application Data

(60) Provisional application No. 61/753,695, filed on Jan. 17, 2013.

(51) Int. Cl.
*A61B 1/12* (2006.01)
*A61B 1/07* (2006.01)

(52) U.S. Cl.
CPC ...... *A61B 1/00059* (2013.01); *A61B 1/00101* (2013.01); *A61B 1/0607* (2013.01); *A61B 1/0646* (2013.01); *A61B 1/07* (2013.01); *A61B 1/127* (2013.01); *A61B 1/128* (2013.01)

(58) Field of Classification Search
CPC ........... A61B 1/06; A61B 1/127; A61B 1/128; A61B 1/00029; A61B 1/00016; A61B 1/00057
See application file for complete search history.

(56) References Cited

U.S. PATENT DOCUMENTS

| | | | |
|---|---|---|---|
| 5,413,092 A | 5/1995 | Williams, II et al. | |
| 5,601,525 A | 2/1997 | Okada | |
| 5,605,532 A | 2/1997 | Schermerhorn | |
| 5,647,840 A | 7/1997 | D'Amelio et al. | |
| 5,740,801 A | 4/1998 | Branson | |
| 5,788,688 A | 8/1998 | Bauer et al. | |
| 5,850,496 A | 12/1998 | Bellahsene et al. | |
| 5,910,106 A | 6/1999 | Morgan et al. | |
| 5,951,543 A | 9/1999 | Brauer | |
| 5,980,816 A | 11/1999 | Suenaga et al. | |
| 6,092,722 A | 7/2000 | Heinrichs et al. | |
| 6,110,107 A | 8/2000 | Bellahsene et al. | |
| 6,293,911 B1 | 9/2001 | Imaizumi | |
| 6,458,078 B1* | 10/2002 | Ludtke | A61B 1/00013 348/E5.029 |
| 6,503,196 B1 | 1/2003 | Kehr | |
| 6,533,721 B1 | 3/2003 | Beutter et al. | |
| 6,638,212 B1* | 10/2003 | Oshima | A61B 1/0002 348/72 |
| 6,689,050 B1 | 2/2004 | Beutter et al. | |
| 6,712,756 B1* | 3/2004 | Kura | A61B 1/00059 600/118 |
| 6,824,539 B2 | 11/2004 | Novak | |
| 7,018,331 B2 | 3/2006 | Chang et al. | |
| 7,289,139 B2 | 10/2007 | Amling et al. | |
| 7,582,056 B2* | 9/2009 | Noguchi | A61B 1/015 600/109 |
| 7,938,774 B2 | 5/2011 | Segawa | |
| 8,029,438 B2 | 10/2011 | Hagihara | |
| 8,083,669 B2 | 12/2011 | Murakami et al. | |
| 8,194,122 B2 | 6/2012 | Amling et al. | |
| 8,597,179 B2 | 12/2013 | Kokubo | |
| 8,657,809 B2 | 2/2014 | Schoepp | |
| 8,725,525 B2 | 5/2014 | Yamaki | |
| 9,247,867 B2 | 2/2016 | Baum et al. | |
| 2004/0064019 A1* | 4/2004 | Chang | A61B 1/00059 600/180 |
| 2007/0286764 A1 | 12/2007 | Noguchi et al. | |
| 2008/0058602 A1* | 3/2008 | Landry | A61B 1/00055 600/180 |
| 2008/0086074 A1 | 4/2008 | Taylor | |
| 2008/0211634 A1* | 9/2008 | Hopkins | A61B 1/00016 340/10.1 |
| 2008/0249355 A1 | 10/2008 | Birnkrant | |
| 2010/0309553 A1 | 12/2010 | Nagamizu | |
| 2011/0092769 A1 | 4/2011 | Kokubo | |
| 2011/0116261 A1 | 5/2011 | Brukilacchio | |
| 2011/0193948 A1* | 8/2011 | Amling | A61B 1/00006 348/68 |
| 2011/0270091 A1* | 11/2011 | Hossack | A61B 1/00059 600/463 |
| 2013/0116507 A1 | 5/2013 | Segawa | |
| 2014/0200406 A1 | 7/2014 | Bennett et al. | |
| 2015/0062317 A1 | 3/2015 | Berci | |
| 2015/0173591 A1 | 6/2015 | Zheng et al. | |
| 2016/0000306 A1* | 1/2016 | Takayama | G02B 23/2484 600/109 |
| 2016/0015247 A1 | 1/2016 | Irion et al. | |

FOREIGN PATENT DOCUMENTS

| | | |
|---|---|---|
| JP | 60095418 A2 | 5/1985 |
| JP | H06-125871 A | 5/1994 |
| JP | H11-47081 A | 2/1999 |
| JP | 2003-334157 A | 11/2003 |
| JP | 2006-191990 A | 7/2006 |

OTHER PUBLICATIONS

Claire Swedberg; Olympus Automates Its Endoscope Tester Via RFID; known before invention (1 page).
"The Olympus Endoscope Drying Cabinet" product brochure, known before invention (4 pages).
Brochure by Olypmus® ; "Reprocessing Management Module" copyrighted in 2013 (5 pages).
Olympus press release dated May 6, 2010 titled "Olympus Develops World's Fastest, Most Compatible Endoscope Reprocessor" (2 pages).
Claire Swedberg; Olympus Automates Its Endoscope Tester Via RFID; dated May 27, 2014 (2 pages).
Extended European Search Report issued in Appln. No. 17203805.1 dated Jun. 4, 2018 (11 pages).

* cited by examiner

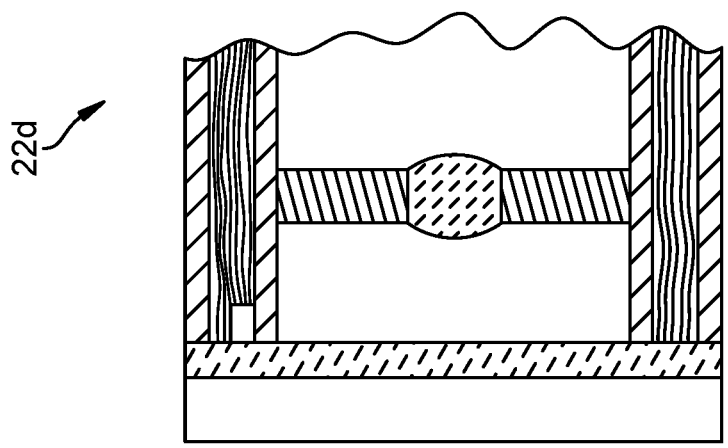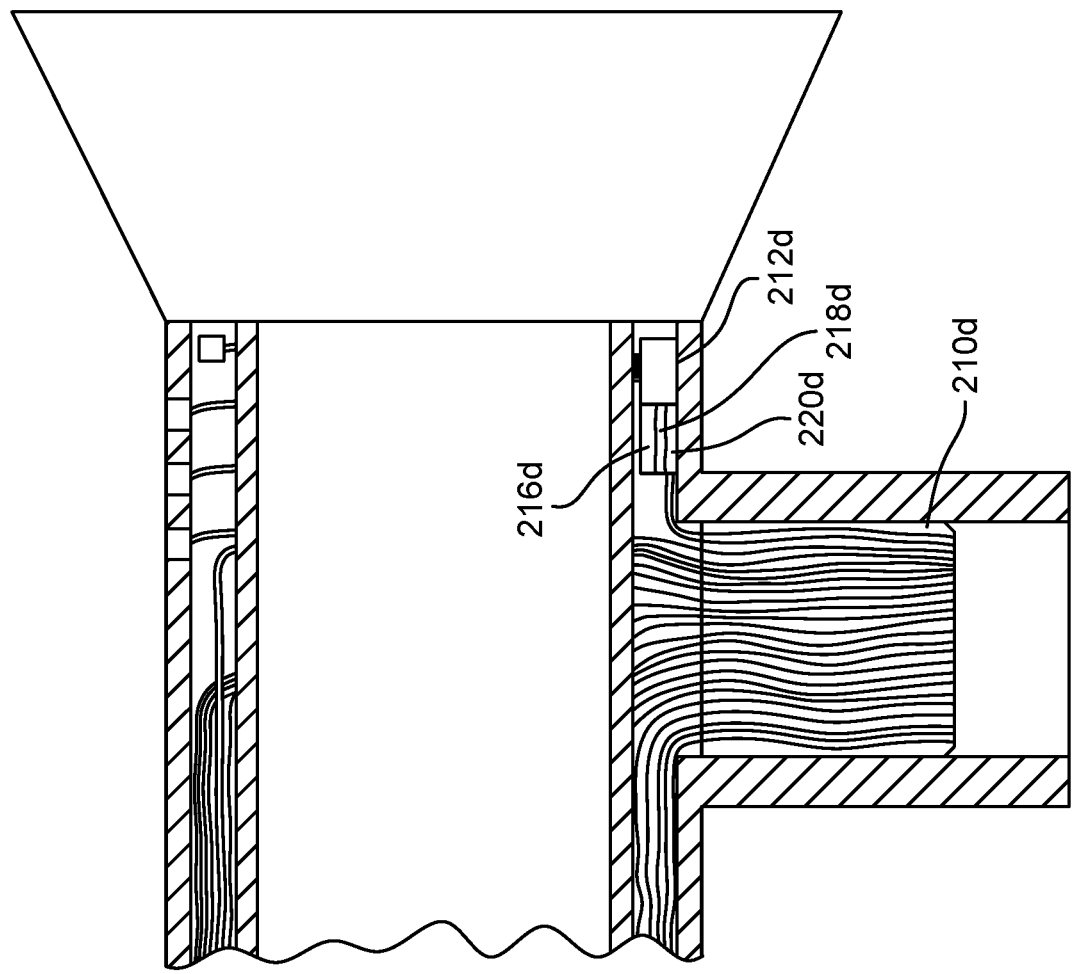
FIG. 13

SYSTEM FOR ALTERING FUNCTIONS OF AT LEAST ONE SURGICAL DEVICE DEPENDENT UPON INFORMATION SAVED IN AN ENDOSCOPE RELATED TO THE ENDOSCOPE

CROSS REFERENCE TO RELATED APPLICATIONS

This is a continuation-in-part of U.S. application Ser. No. 14/155,480 entitled ANTI-FOGGING DEVICE FOR ENDOSCOPE, filed Jan. 15, 2014, which claims the benefit of U.S. Provisional Application Ser. No. 61/753,695 entitled ANTI-FOGGING DEVICE FOR ENDOSCOPE, filed Jan. 17, 2013, both of which are incorporated herein by reference in their entirety.

FIELD OF THE INVENTION

The present invention relates to relaying information related to an endoscope to other operating room devices.

BACKGROUND OF THE INVENTION

An endoscope is a surgical tool designed to be placed inside a body in order to provide a view of the interior portion of the body. In endoscopic surgery, the endoscope is placed in the body at the location at which it is necessary to perform a surgical procedure. Other surgical instruments are placed in the body at the surgical site. The surgeon views the surgical site through the endoscope in order to assess the interior portion of the body and to manipulate the other surgical instruments to perform the desired surgical procedure. The development of endoscopes and their companion surgical instruments has made it possible to perform minimally invasive surgery that eliminates the need to make a large incision in the patient to gain access to the surgical site. Instead, during endoscopic surgery, small openings, called portals, are formed. One advantage of performing endoscopic surgery is that since the portions of the body that are cut are reduced, the portions of the body that need to heal after the surgery are likewise reduced. Still another advantage of endoscopic surgery is that it exposes less of the interior tissue of the patient's body to the open environment. This minimal opening of the patient's body lessens the extent to which the patient's internal tissue and organs are open to infection.

Surgeons have used many devices along with the endoscope to help them during operative procedures. In the past, surgeons or other people in the operative theater have had to individually adjust the settings for each device in the operative theater before surgery. An easier method of adjusting the settings of devices in an operative theater is desired.

SUMMARY OF THE INVENTION

The present invention, according to one aspect, is directed to an endoscopic system including an endoscope having saved information therein related to the endoscope, a light source console for providing light to the endoscope, and a light cable connected between the endoscope and the light source console. The light cable is configured to communicate the light from the light source console to the endoscope. The information related to the endoscope is relayed from the endoscope to the light source console through the light cable for altering functions of at least one of the light source console and an auxiliary device.

Another aspect of the present invention is to provide an endoscopic system including an endoscope having saved information therein related to the endoscope, a light source providing light to the endoscope, and a light cable connected between the endoscope and the light source. The light cable communicates the light from the light source console to the endoscope along with communicating the information related to the endoscope to the light source console. The information related to the endoscope is wirelessly relayed from the endoscope to the light cable. Functions of at least one of the light source console and an auxiliary device are altered dependent upon the information related to the endoscope.

Yet another aspect of the present invention is to provide a method of altering functions of at least one surgical device. The method includes saving information related to an endoscope within the endoscope, providing a light source console, connecting a light cable between the endoscope and the light source console, providing light to the endoscope from the light source console via the light cable, relaying the information related to the endoscope from the endoscope to the light source console through the light cable, and altering functions of the at least one surgical device dependent upon the information related to the endoscope.

BRIEF DESCRIPTION OF THE DRAWINGS

One or more embodiments of the present invention are illustrated by way of example and should not be construed as being limited to the specific embodiments depicted in the accompanying drawings, in which like reference numerals indicate similar elements.

FIG. 13 is a schematic view of a second embodiment of a communicating endoscope of the present invention.

Certain terminology will be used in the following description for convenience in reference only, and will not be limiting. For example, the words "forwardly" and "distally" will refer to the direction toward the end of the arrangement which is closest to the patient, and the words "rearwardly" and "proximally" will refer to the direction away from the end of the arrangement which is furthest from the patient. Said terminology will include the words specifically mentioned, derivatives thereof, and words of similar import.

DETAILED DESCRIPTION

Figure 1:
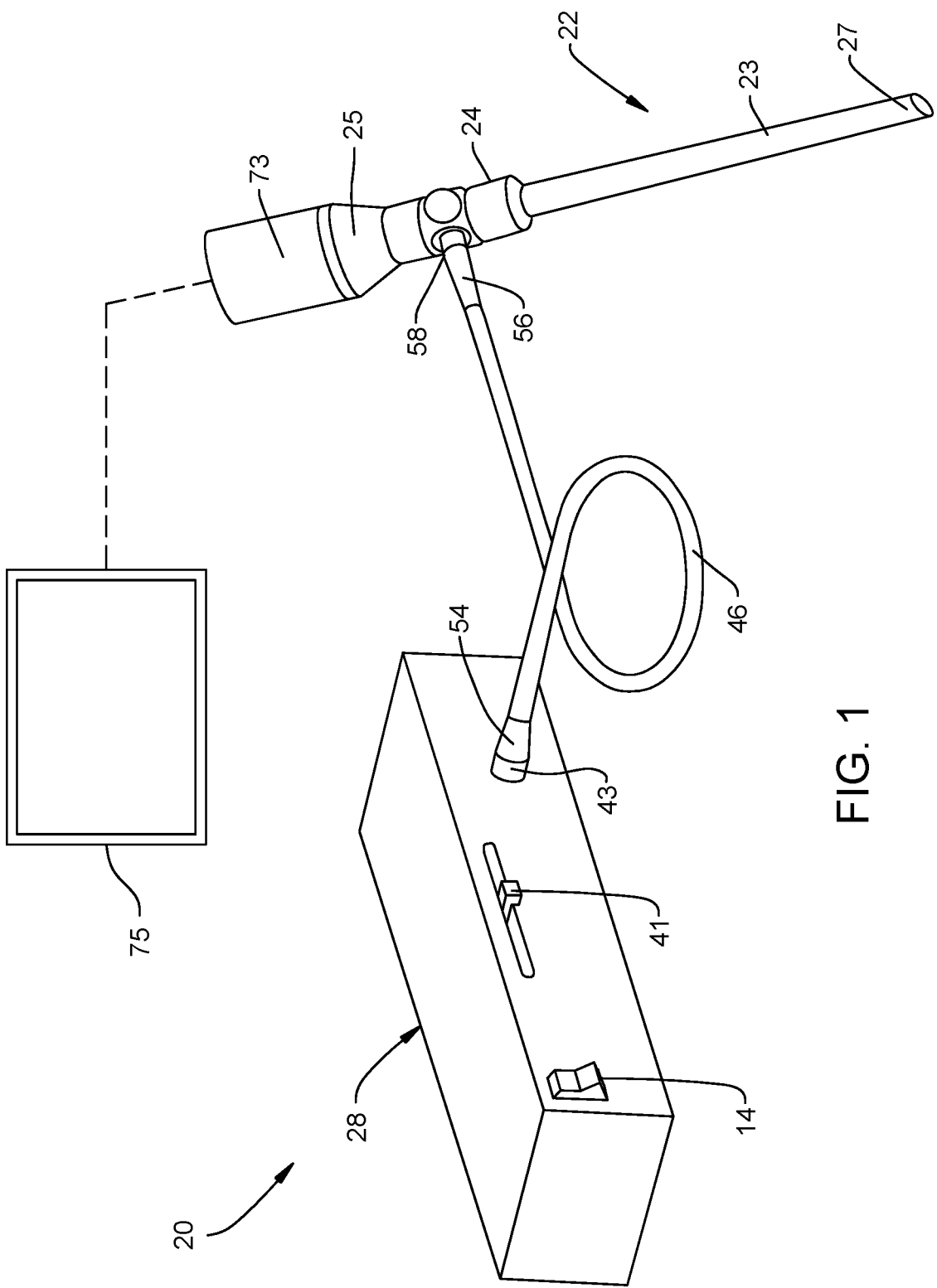
FIG. 1 illustrates a perspective schematic view of an endoscopic system according to the invention.

FIG. 1 illustrates an endoscopic system 20 including an endoscope 22, a transmission cable 46, and a light source console 28. The endoscope 22 is defined by an elongated and generally hollow shaft 23 with a distal end 27 configured for insertion within a body cavity. The hollow shaft 23 also has a proximal end 24 which mounts thereon an eyepiece 25 fitted to provide a viewing port through which the surgeon views the surgical field (for example, directly or through a connection between a viewing port, a digital camera 73, and a display screen 75). A light port 58 may be connected with light inputs to selectively transmit light to a target via the endoscope 22. In the illustrated embodiment, the light source console 28 sends electromagnetic waves to the distal end 27 of the endoscope 22 to heat the same to prevent fogging.

The light source console 28 selectively provides electromagnetic radiation as imaging light for use in the operating theater for illuminating the surgical field. In the present embodiment, the candlepower of the imaging light emitted from the light source console 28 is selectively adjustable through manipulation of a sliding switch 41. The light source console 28 also provides electromagnetic radiation as heating light to the distal end 27 of the endoscope 22 to prevent fogging of the same as discussed in more detail below. Further, the light source console 28 comprises a socket 43 to transmit the electromagnetic radiation from the light source console 28 to instruments such as the endoscope 22 via intermediary devices, such as the transmission cable 46.

The illustrated transmission cable 46 is configured to transmit light from a proximal end 54 of the transmission cable 46 to a distal end 56 of the transmission cable 46 attached to the light port 58. The transmission cable 46 can comprise an optical fiber or optical fibers suited to transmit electromagnetic radiation via total internal reflection of such radiation within the fiber material. The proximal end 54 and the distal end 56 include terminal geometries, such as plugs, conducive to receiving and emitting, respectively, electromagnetic radiation.

Figure 2:
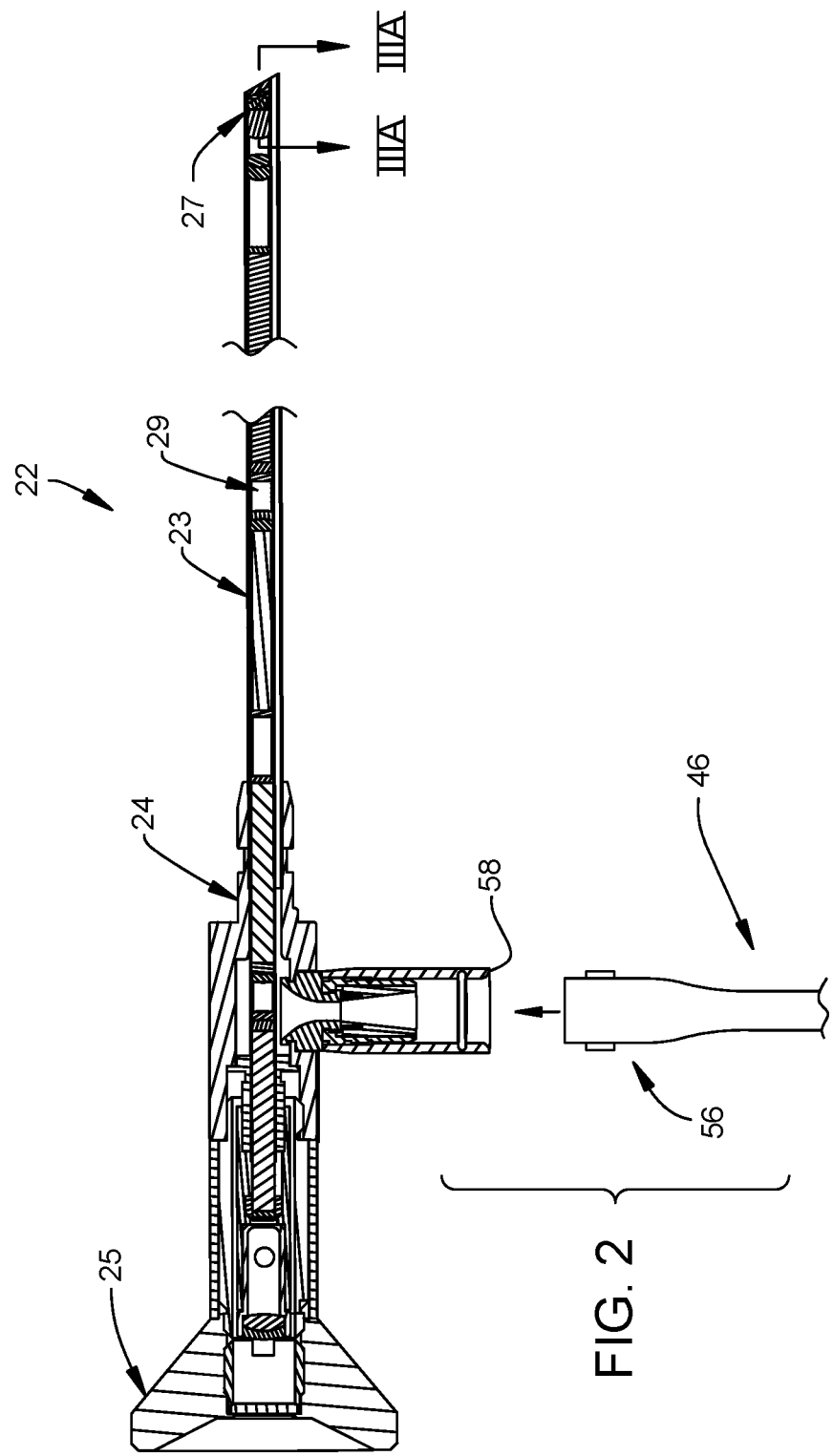
FIG. 2 is an enlarged longitudinal and fragmentary cross-sectional view of the endoscope of FIG. 1, and a fragmentary view of the distal end of the cable associated with the light source.

As shown in FIG. 2, the endoscope 22 contains a variety of internal mechanisms. For example, the shaft 23 houses therein an imaging arrangement, which in this embodiment includes an optical train 29 comprised of one or more lenses suitably aligned to transmit an image from the distal end 27 to the eyepiece 25. The shaft 23 incorporates therein suitable mounting structures which maintain alignment of the components of the optical train 29 toward the eyepiece 25, and includes the light port 58 whereby electromagnetic radiation may be transmitted into the endoscope 22 via the transmission cable 46. While the endoscope 22 is illustrated as being rigid, it is contemplated that the endoscope could be rigid, semi-rigid or flexible.

Figure 3:
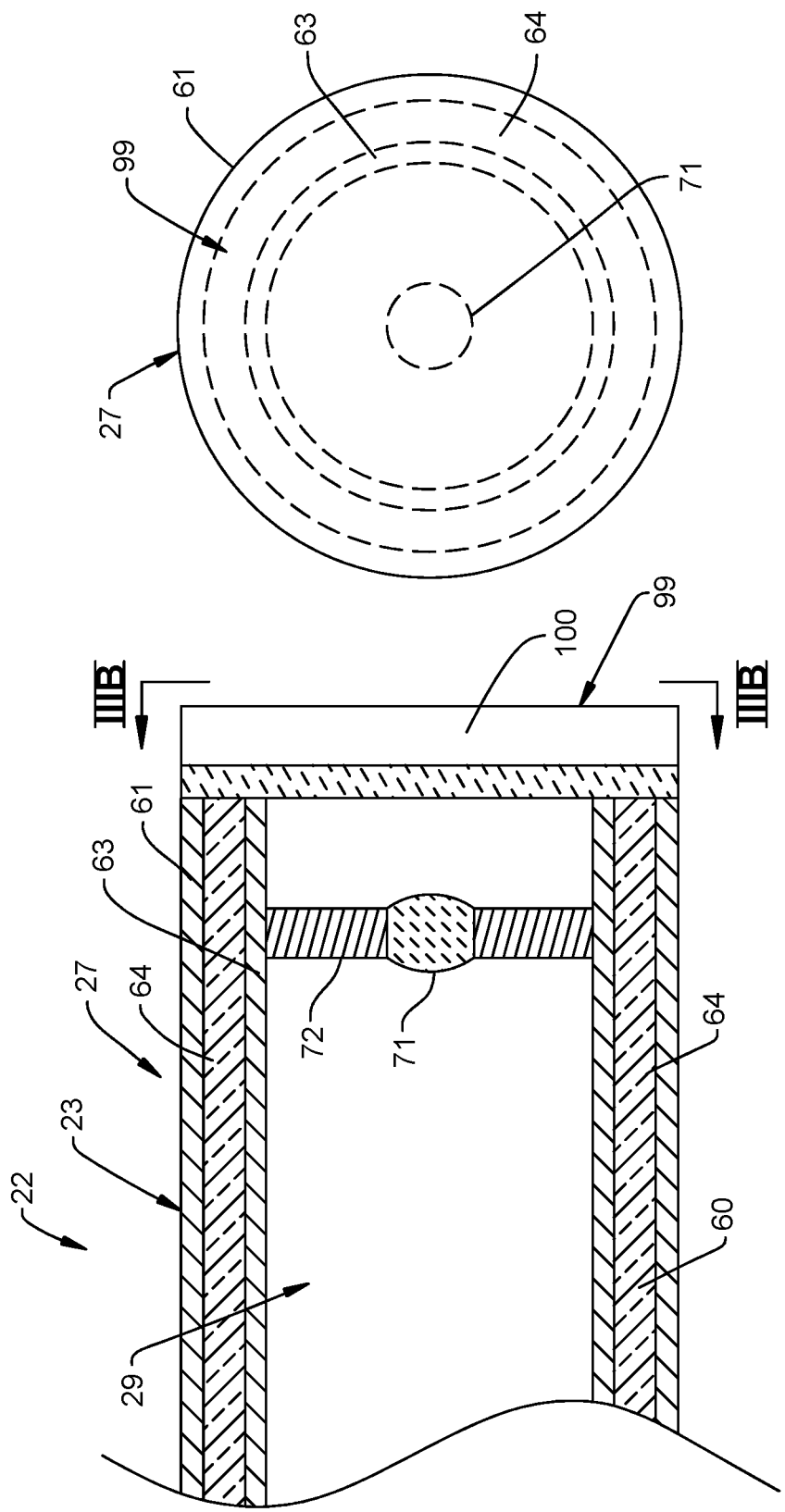
FIG. 3A is an enlarged, longitudinal and fragmentary cross-sectional view of the distal end of the endoscope of FIG. 1 as seen generally along line IIIA-IIIA in FIG. 2.
FIG. 3B is an enlarged end view of the distal end of the endoscope as seen generally along line IIIB-IIIB in FIG. 3A.

FIGS. 3A and 3B illustrate the structure of the endoscope 22 in greater detail at the distal end 27 thereof. The shaft 23 of the endoscope 22 is defined by a substantially cylindrical and tubular outer housing 61 and an inner tubular housing 63 located within the outer housing 61. The outer and inner housings 61, 63 are sized such that an annular space 60 is defined therebetween which extends along a substantial portion of the longitudinal extent of the shaft 23. A cylindrical optical fiber 64 is located within the annular space 60 and extends from the distal end 27 rearwardly to the proximal end 24 of the endoscope 22 to receive electromagnetic radiation transmitted into the endoscope 22 via the transmission cable 46.

In the illustrated example, the inner tubular housing 63 encloses innermost functional components of the endoscope 22, such as the optical train 29. The optical train 29 can comprise an image lens 71 at the distal end 27 suitably fixed or connected to the inner surface of the inner tubular housing 63 with a corresponding generally annular image lens casing 72. A distal window 99 is located at the distal terminus of the tubular outer housing 61, the inner tubular housing 63 and the optical fiber 64. In one embodiment, the otherwise empty spaces in the optical train 29, for instance the space between the image lens 71 and the distal window 99, are hermetically sealed against the exterior of the endoscope 22 and filled with a specified fluid such as low-humidity nitrogen gas. Alternatively, one or more such spaces may be hermetically sealed with respect to the exterior of the endoscope 22 and substantially devoid of fluid. The components and workings of the endoscopic system 20 as described above are conventional and further description is accordingly not provided herein.

The illustrated endoscope 22 includes the distal window 99 on the distal end 27 thereof. The distal window 99 allows the imaging light coming from the optical fiber 64 to pass therethrough for illuminating the surgical field. After passing through the distal window 99, the imaging light reflects off of matter in the surgical field and reflects back through and into the endoscope 22 through a center area of the distal window 99 to be passed to the eyepiece 25. The distal window 99, however, does not allow the heating light to pass therethrough in order to absorb energy of the heating light to heat the distal window 99. Heating of the distal window 99 prevents moisture from condensating on an exterior surface 100 of the distal window 99, thereby preventing fogging of the endoscope 22. The distal window 99 can comprise an optical absorbing element or an optical absorbing element in combination with another optical element (e.g., a fully transparent window).

Figure 6:
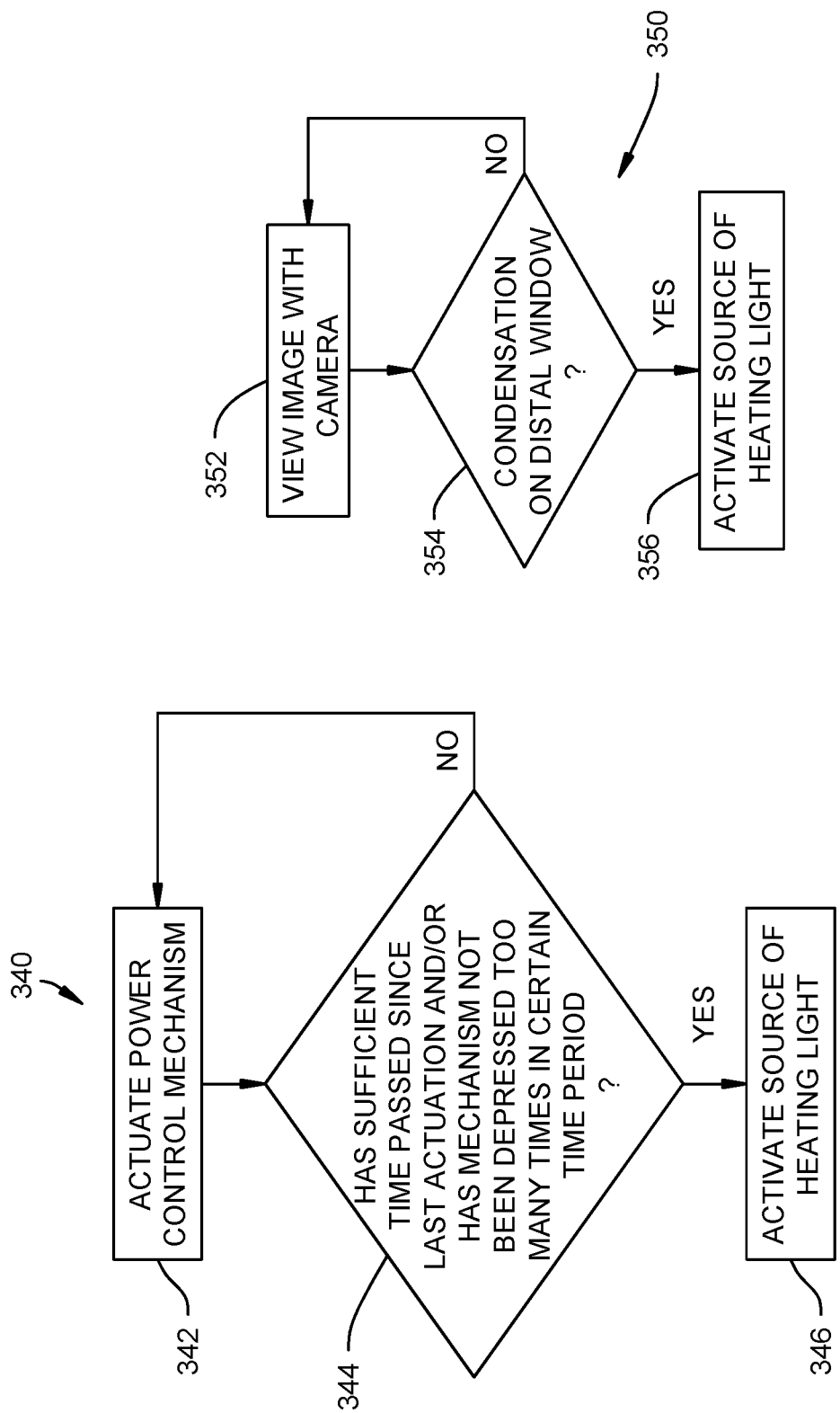
FIG. 6 is a schematic view of the endoscope system according to the present invention illustrating a sensor for reading a temperature of a distal window of the endoscope.

In the illustrated example, the imaging light can come from a standard, unmodified source 102 of imaging light and the heating light is generated from a source 104 of heating light which adds infrared ("IR") light (broad or narrow band) thereto (see FIG. 6). The light source console 28 thereby supplies the endoscope 22 with typical imaging light (e.g., visible light) and heating light in the form of IR light. The endoscope 22 thereby emits imaging light to illuminate an inside of the body cavity at the distal end 27 thereof and the distal window 99 prevents condensation by quickly reaching body temperature through absorbing IR radiation from the IR light. In the present example, it is contemplated that the desired temperature of the distal window 99 is approximately body temperature.

It is contemplated that the distal window 99 could absorb specific bands or the entire IR band. For example, the heating light could come from a narrow-band IR laser source (i.e., the source 104 of heating light in this example) and the distal window 99 could be an absorbing band-stop, optically transparent IR filter. With the heating light coming from a narrow-band IR laser source and the distal window 99 being an absorbing band-stop, optically transparent IR filter, the remainder of the IR band can be available for use in current and future IR imaging products and technologies. It is contemplated that the choice of light bandwidths for the heating light and the imaging light can be flexible. With an appropriate choice of camera, imaging light, heating light, and optics, an aspect of the present invention is to be fully capable of being compatible with endoscopy imaging systems using any choice of bandwidth throughout the ultraviolet, visible, and IR portion of the electromagnetic spectrum. The heating light may also be selected from any part of this spectrum, and can be chosen from outside of the imaging band in a region that can be absorbed by inexpensive window optics while passing the imaging bandwidth (which allows the window temperature and illumination brightness to be independently adjusted). In one embodiment, the distal window 99 captures visible-light imagery and uses broadband infrared light in the mid-IR range and is also fully capable of acquiring near IR-imagery. It is contemplated that the distal window 99 can include a thickness of approximately 0.5 mm and have a diameter of about 0.5 mm to allow the distal window 99 to heat quickly and thoroughly without producing reflections of the imaging light which enters the distal window 99.

Figure 4:
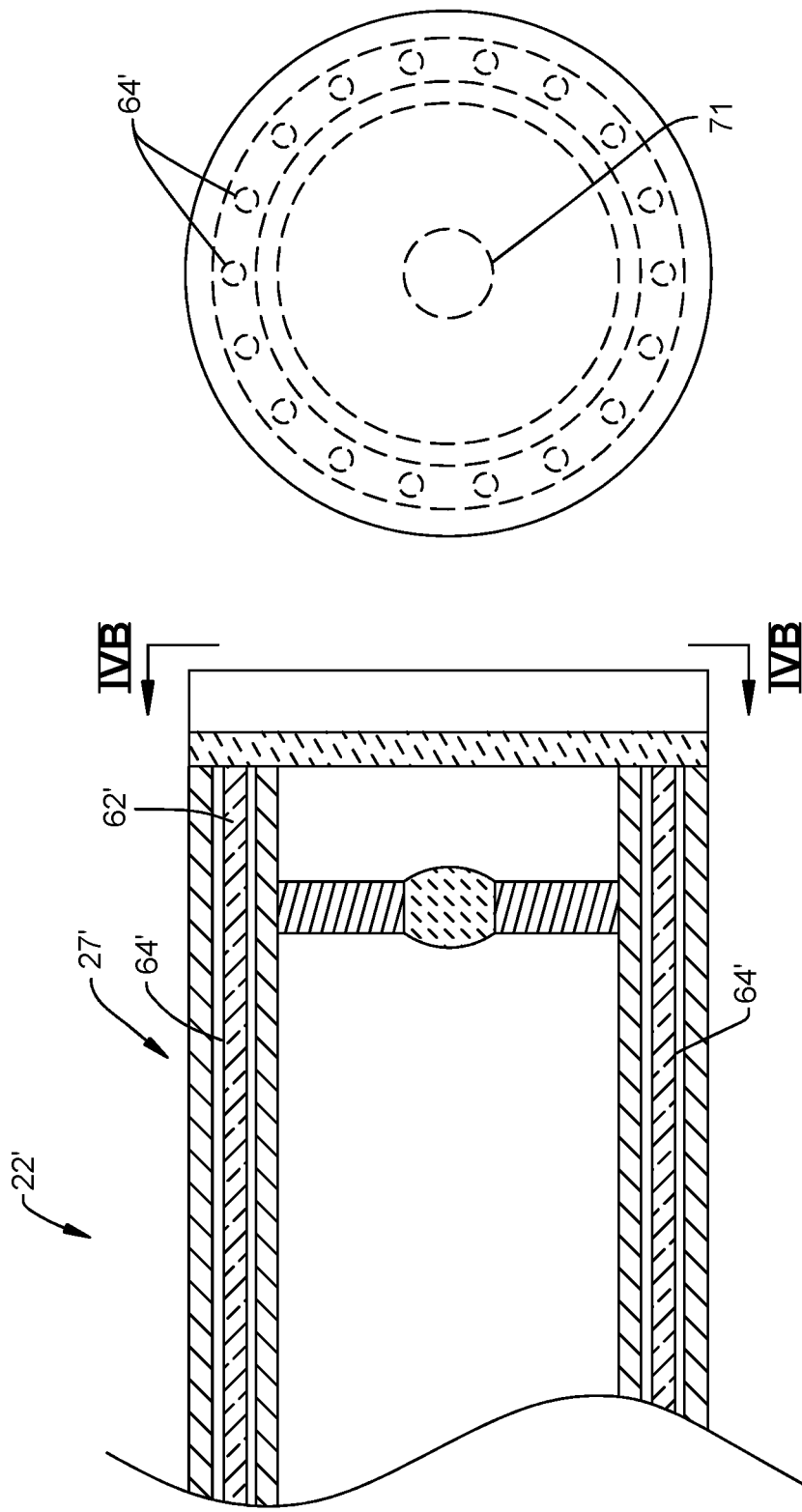
FIG. 4A is an enlarged, longitudinal and fragmentary cross-sectional view of the distal end of an alternative endoscope.
FIG. 4B is an enlarged end view of the distal end of the alternative endoscope as seen generally along line IVB-IVB in FIG. 4A.

FIGS. 4A and 4B illustrate an alternative embodiment for the endoscope 22', including a plurality of optical fibers 64' formed into a circle with the distal end 27' including a ring 62' containing therein distal ends of the respective optical fibers 64'. In one embodiment, the ring 62' is defined by an adhesive which serves to fix the ends of the optical fibers 64' at the distal end 27' of endoscope 22' such that the ends of the optical fibers 64' are disposed in a generally annular fashion about the distal end 27' for emitting light on the surgical site. For example, the ring 62' may bind together a plurality of optical fibers 64' into a solid annular mass via adhesives that do not substantially impair the transmissive properties of the optical fibers 64'.

Operation

The endoscope 22 is connected to the light source console 28 via the transmission cable 46. Specifically, the transmission cable 46 attaches to the light source console 28 at the interface between the socket 43 and the proximal end 54 and the transmission cable 46 attaches to the endoscope 22 at the interface between the light port 58 and the distal end 56. In one embodiment, the eyepiece 25 is operationally connected to an image sensor assembly or camera 73 comprising a CCD (charged coupled device) or CMOS sensor (complementary metal oxide semiconductor), which image sensor assembly provides the surgeon with a view of the surgical site on the display screen 75 (or a plurality of displays). Such an image sensor assembly or camera 73 may, for example, be provided at the proximal end 24 of the endoscope 22, adjacent the eyepiece 25. The distal end 27 of the shaft 23 is inserted into the body cavity of the patient. Light is cast on the target area through actuation of a switch 14 on the light source console 28 and corresponding transmission of electromagnetic radiation from the light source console 28, through the transmission cable 46 and out the annular ring 62 of the optical fiber 64 or optical fibers 64' of the endoscope 22. Electromagnetic radiation in the form of imaging light at least partially reflects off the target area and the reflected light passes through the distal window 99, down the optical train 29, and into the eyepiece 25. Furthermore, the heating light is absorbed by the distal window 99 to prevent condensation by quickly reaching body temperature through absorbing IR radiation from the IR light.

Power Level

An aspect of the present invention is to limit the power level of the source 104 of the heating light (and thereby the heating light) to limit the temperature of the distal window 99. A first approach is to maintain the source 104 of heating light at a constant power level that defogs or prevents fogging of the distal window 99 with sufficient speed and consistency, which is illustrated in the single method step 300 of FIG. 5A. It is contemplated that the method step 300 may employ knowledge of the endoscope 22 attached to the light source console 28 that is provided either manually by the user or automatically by transmission of heating parameters via radiofrequency or infrared light or other means from the endoscope 22 to the light source console 28. In the latter case, the parameters may be specific to the endoscope 22 or parameters specific to the individual endoscope 22 being used, with the parameters being measured in a factory during manufacture of the endoscope 22.

Figure 5:
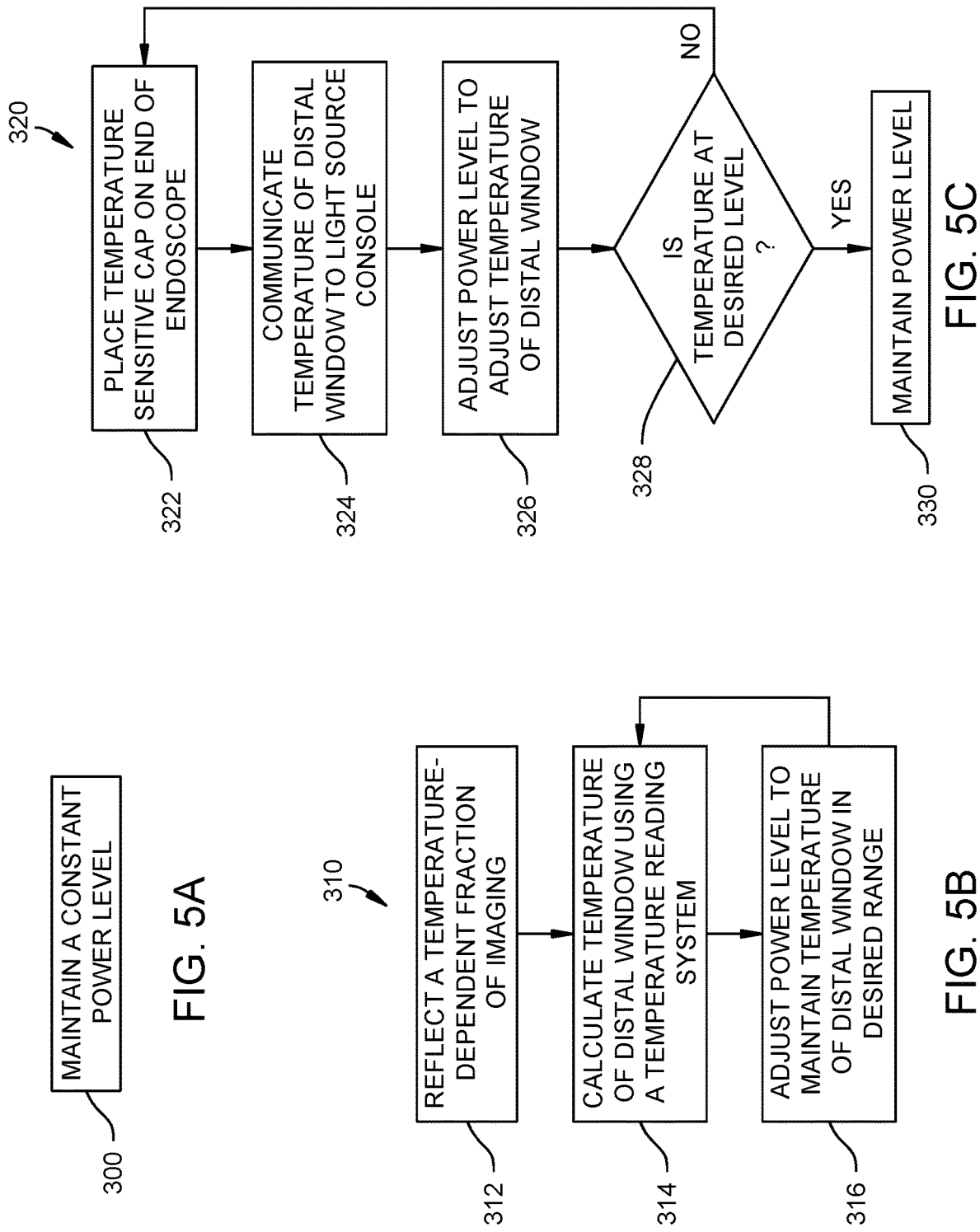
FIGS. 5A-5E illustrate flow charts for approaches for setting a power level of a source of heating light of the present invention.

A second approach for limiting the temperature of the distal window 99 includes a method 310 of measuring a temperature of the distal window 99 to ensure that the distal window 99 does not rise above a desired temperature (see FIG. 5B). FIG. 6 illustrates the endoscopic system 20 of the present invention including the light source console 28, the transmission cable 46 and the endoscope 22. The light source console 28 includes the source 102 of imaging light and the source 104 of heating light. The light source console 28 also includes a mirror 106 therein that reflects the heating light coming from the source 104 of heating light into a path of the imaging light coming from the source 102 of imaging light.

In the illustrated method 310 of measuring a temperature of the distal window 99 of the second approach, the distal window 99 will reflect a temperature-dependent fraction of the imaging light back to the light source console 28 at step 312 (e.g., by having the distal window include a Bragg grating filter). The temperature-dependent fraction of the imaging light sent back to the light source console 28 will reflect off of the mirror 106 and be sent to a temperature reading system 108, wherein the temperate of the distal window 99 is calculated using the temperature reading system 108 at step 314. It is contemplated that the temperature reading system 108 can comprise a single or multiple photodiodes with or without additional optical fibers or a spectrometer system. The temperature reading of the distal window 99 made by the temperature reading system 108 is used to modulate the heating light output from the source 104 of heating light to bring the distal window 99 to a desired temperature and to prevent overheating of the distal window 99 at step 316. The method 310 of measuring a temperature of the distal window 99 can continuously monitor the temperature of the distal window 99 at step 314 to continuously adjust the power level of the source 104 of heating light to maintain the desired temperature.

Figure 7:
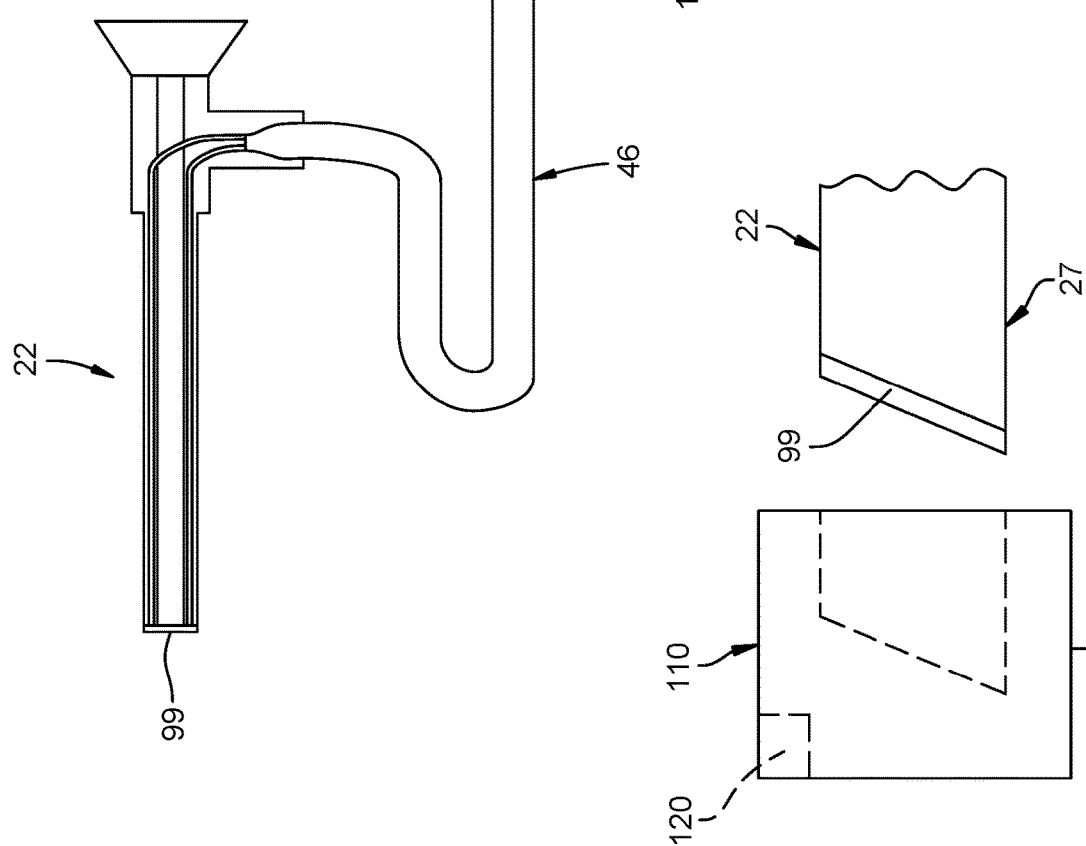
FIG. 7 is a side view of a distal end of the endoscope of the present invention configured to have a cap placed thereon.

A third approach for controlling the power level and temperature of the distal window 99 includes using a temperature sensitive cap 110 configured to be positioned over the distal end 27 of the endoscope 22 (FIG. 7) in a method 320 of measuring a temperature of the distal window 99 (see FIG. 5C). The method 320 of measuring a temperature of the distal window 99 includes positioning the temperature sensitive cap 110 over the distal end 27 of the endoscope 22 for a short period of time (e.g., few seconds) before the distal end 27 of endoscope 22 is positioned within the body cavity at step 322.

The illustrated temperature sensitive cap 110 positioned over the distal end 27 of endoscope 22 reports the temperature of the distal window 99 to the light source console 28 (or control system thereof) over a communication network 112 at step 324. As the temperature of the distal window 99 reaches the desired temperature (e.g., body temperature), a controller (e.g., proportional-integral-derivative (PID) controller) in the light source console 28 (or control system thereof) engages a control loop to compute the power needed at the source 104 of heating light to maintain the desired temperature (e.g., body temperature). The communication network 112 can be temperature sensitive RFID technology that reports the temperature of the distal window 99 to the light source console 28 (or control system thereof). Alternatively, temperature sensors could be located within the temperature sensitive cap 110 for measuring the temperature of the distal window 99 that communicates the temperature of the distal window 99 to the light source console 28 (or control system thereof) via a wired or wireless communication network 112. It is contemplated that one method of communication may be to send infrared signals from the cap 110 back through the endoscope 22, through the transmission cable 46, and back to the light source console 28, with a detector in the light source console interpreting the infrared signals to determine the temperature of the distal window 99. It is contemplated that the temperature reading sent to the light source console 28 could be above a desired temperature such that the light source console (of control system thereof) turns off the source of heating light. The RFID technology or the temperature sensors can be passively powered or can be actively powered by a power source 120 within the temperature sensitive cap 110. The power source 120 can be a battery or a photoelectric solar cell than extracts energy from imaging light coming from the light source console 28 and out of the endoscope 22 through the distal window 99. It is contemplated that the temperature sensitive cap 110 can be disposable and/or sterilizable (e.g., by autoclaving).

In the illustrated example, the method 320 of measuring the temperature of the distal window 99 using the temperature sensitive cap 110 includes adjusting the power level of the source 104 of heating light to adjust the temperature of the distal window 99 at step 326. If the temperature of the distal window 99 is determined to be at the desired level at step 328, the power level of the source 104 of heating light is maintained at step 330. If the temperature of the distal window 99 is determined to not be at the desired level at step 328, the temperature sensitive cap 110 remains on the endoscope 22 and the method 320 of measuring the temperature of the distal window 99 returns to step 322.

Figure 8:
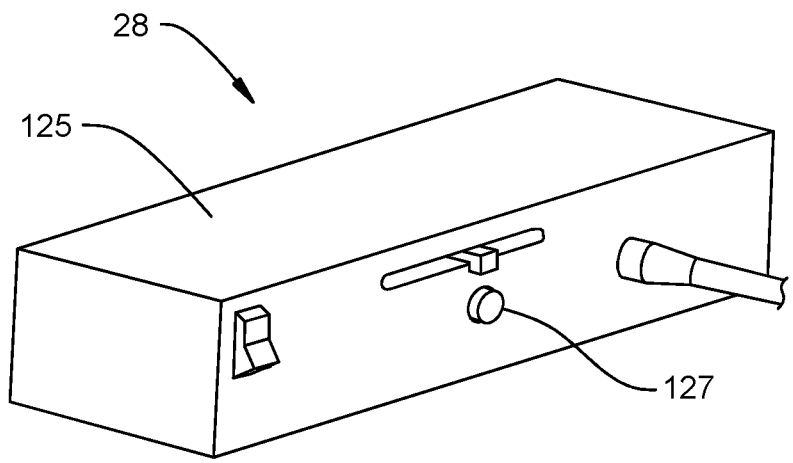
FIG. 8 is a perspective view of a console or light source of the endoscopic system having a button thereon.

A fourth approach for controlling the power level and temperature of the distal window 99 includes using a user activated trigger or control in a method 340 of powering the source 104 of heating light (FIG. 5D). For example, FIG. 8 illustrates the light source console 28 having a housing 125 with a control mechanism 127 thereon. The control mechanism 127 can be a button that is depressed for activating the source 104 of heating light for a finite amount of time. The method 340 of powering the source 104 of heating light includes actuating the control mechanism 127 at step 342. It is contemplated that the control system for the light source console 28 and/or the source 104 of heating light could track the number and/or frequency of depressions of the button to honor not more than a selected number of depressions within a certain time frame to prevent overheating of the distal window 99 at step 344. If the control mechanism 127 has not been depressed too many times in a certain time period, the source 104 of heating light is activated at step 346. It is contemplated that the control mechanism 127 could be a dial (or slider or similar mechanism) that controls the power of the source 104 of heating light (e.g., higher power or lower power as the dial is moved or from a "temperature maintenance" power level to a higher "heating" power level and vice/verse as the dial is moved). It is contemplated that the control system for the light source console 28 and/or the source 104 of heating light could automatically turn down the power level after a certain time period or after a certain amount of power has been transmitted to the endoscope 22.

A fifth approach for controlling the power level and temperature of the distal window 99 includes a method 350 of using the camera to activate or modulate the control system for the light source console 28 and/or the source 104 of heating light when fog or condensation is detected by the camera 73 as being on the distal window 99 (FIG. 5E). In the method 350 of controlling the power level using the camera 73, the image is viewed by the camera 73 at step 352. If fog or condensation is determined to be on the camera 73 at step 354, the source 104 of heating light is activated at step 356. If fog or condensation is determined to be on the camera 73 at step 354, the method 350 of controlling the power level using the camera 73 returns to step 352 to view the image again using the camera 73. Fog or condensation can be detected by the camera 73 as being on the distal window 99 using an image-processing analysis.

Heating Window Sensing

An aspect of the present invention is to detect if the endoscope 22 has a distal window 99 in order to prevent supplying heating light to the endoscope 22 if the endoscope 22 does not have the distal window 99. If the endoscope 22 does not have a distal window 99, the heating light would pass through the endoscope 22 and into the patient.

Figure 9A:
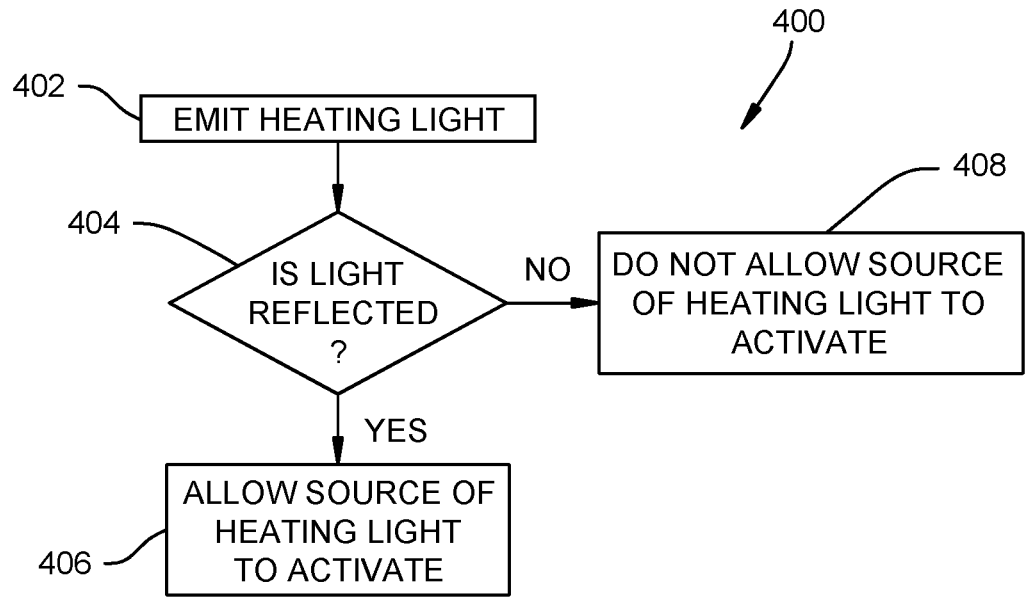
FIGS. 9A-9D illustrate flow charts for methods for determining if an endoscope includes a distal window of the present invention.
Figure 10:
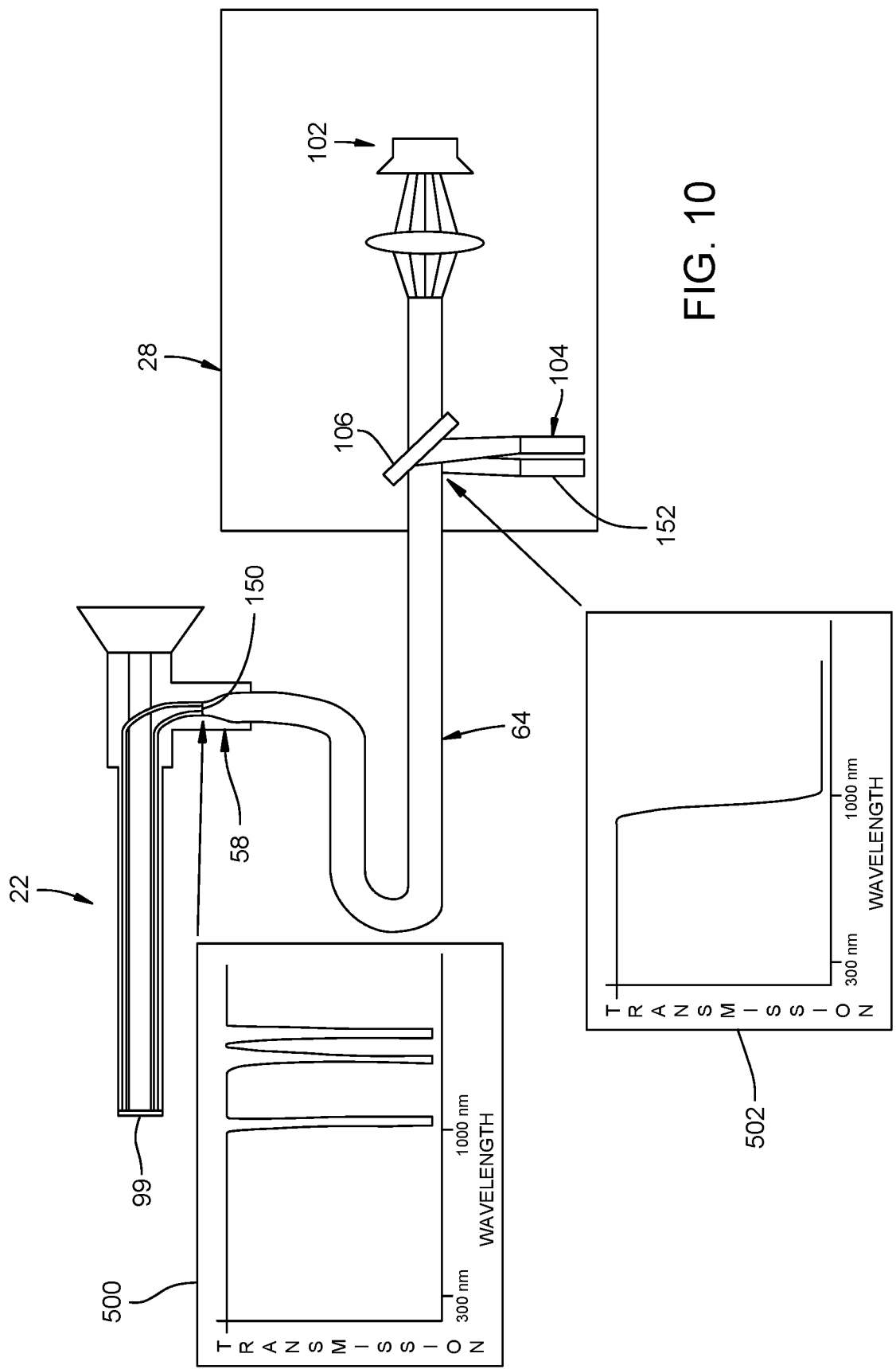
FIG. 10 is a schematic view of the endoscope system according to the present invention illustrating a detector for detecting reflection of a band of light from the endoscope.

A first method 400 (FIG. 9A) for determining if the endoscope 22 includes the distal window 99 is to place a partially reflective optical coating or mirror 150 at the light port 58 of the endoscope 22. As illustrated in FIG. 10, the partially reflective optical coating or mirror 150 could have a narrow band of reflectivity or multiple narrow bands of reflectivity of light as illustrated in graph 500. For example, the partially reflective optical coating or mirror 150 could have a narrow band of reflectivity or multiple narrow bands of reflectivity on the order of single digit nanometer wavelengths. The first method 400 (FIG. 9A) for determining if the endoscope 22 includes the distal window 99 comprises emitting heating light with the source 104 of heating light at step 402. The electromagnetic waves reflected off of the partially reflective optical coating or mirror 150 could be reflected off of the mirror 106 that only allows light of certain wavelengths to pass therethrough as shown in graph 502 within the light source console 28 in order to be read by a detector 152 at step 404. The partially reflective optical coating or mirror 150 can allow the imaging light to pass therethrough as illustrated in graph 502 of FIG. 10.

Using the illustrated first method 400, the control system for the light source console 28 and/or the source 104 of heating light will allow the source 104 of heating light to activate if the detector 152 senses the light reflected from the partially reflective optical coating or mirror 150 at step 406. However, if the detector 152 does not sense the light reflected from the partially reflective optical coating or mirror 150 at step 408, the control system for the light source console 28 and/or the source 104 of heating light will not allow the source 104 of heating light to activate. Therefore, if the endoscope 22 does not have the partially reflective optical coating or mirror 150, the source 104 of heating light will not activate.

In an embodiment of the first approach for determining if the endoscope 22 includes the distal window 99, the source 104 of heating light can send out lower power IR sense pulses dichroically mixed with the imaging light leading to the endoscope 22. Reflections of the IR sense pulses are detected by the detector 152, which is capable of distinguishing multiple bands of light and the intensities of the light. It is contemplated that the band or bands of reflected light can be used to identify the type and/or manufacturer of the endoscope 22 and the control system for the light source console 28 and/or the source 104 of heating light would only be activated when a particular type and/or manufacturer of the endoscope 22 is identified in order to prevent overheating of the distal window 99. Alternatively, the control system for the light source console 28 and/or the source 104 of heating light could be altered depending on the particular type and/or manufacturer of the endoscope 22 identified. It is also contemplated that the light source console 28 could communicate with the camera 73 or the display screen 75 or control thereof to optimize the image passed through the endoscope 22 depending on the particular type and/or manufacturer of the endoscope 22 identified.

Figure 9B:
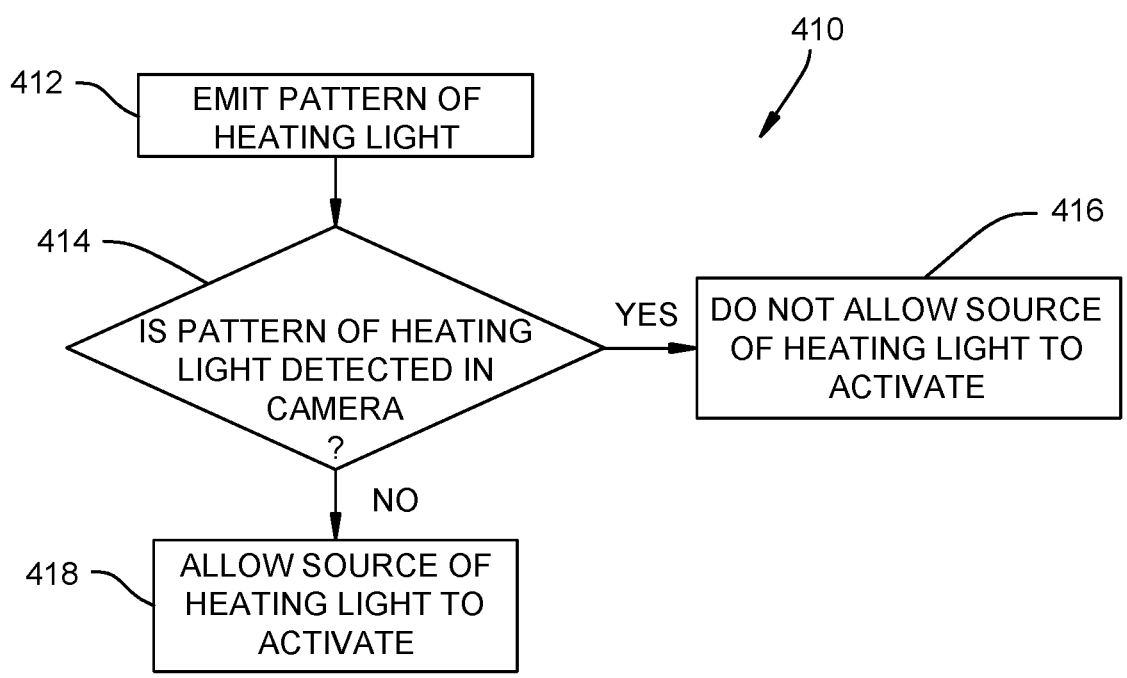

A second method 410 (FIG. 9B) for determining if the endoscope 22 includes the distal window 99 is to emit a pattern of electromagnetic waves with the light source console 28 at step 412, send the pattern of electromagnetic waves through the endoscope 22 and have the camera or control thereof look for the pattern. If the camera or control thereof identifies the pattern at step 414, then the camera 73 or control thereof sends a signal to the light source console 28 indicating that the endoscope 22 does not have the distal window 99, thereby not allowing the source 104 of heating light to activate at step 416. Conversely, if the camera 73 or control thereof does not identify the pattern at step 414, then the camera 73 or control thereof sends a signal to the light source console 28 indicating that the endoscope 22 does have the distal window 99 such that the heating light can be emitted by the light source console 28 at step 418.

For example, the light source console 28 can emit IR light (from the source 104 of heating light or from another source) up to about 800 nm wavelength, with the distal window 99 preventing passage of electromagnetic waves having a wavelength greater than 700 nm. It is contemplated that the source 104 of heating light could be an LED. If the camera 73 or control thereof senses light having a wavelength between 700 nm and 800 nm, then the camera 73 or control thereof will instruct the light source console 28 to turn off the source 104 of heating light because the endoscope 22 does not have the distal window 99. However, if the camera 73 or control thereof senses light having a wavelength between 700 nm and 800 nm, then the camera or control thereof will instruct the light source console 28 to use the source 104 of heating light because the endoscope 22 does have the distal window 99. It is contemplated that the second method 410 for determining if the endoscope 22 includes the distal window 99 could be used in conjunction with a scope-detection technique to ensure that the endoscope 22 with the distal window 99 is being used. It is contemplated that the pattern of electromagnetic waves could be sent to be sensed (or not sensed as the case may be) continuously, only at the beginning of use of the endoscope 22 or periodically to establish higher confidence of use of the endoscope 22 with the distal window 99 and to detect any change in the endoscope 22 during a surgical procedure.

Figure 9C:
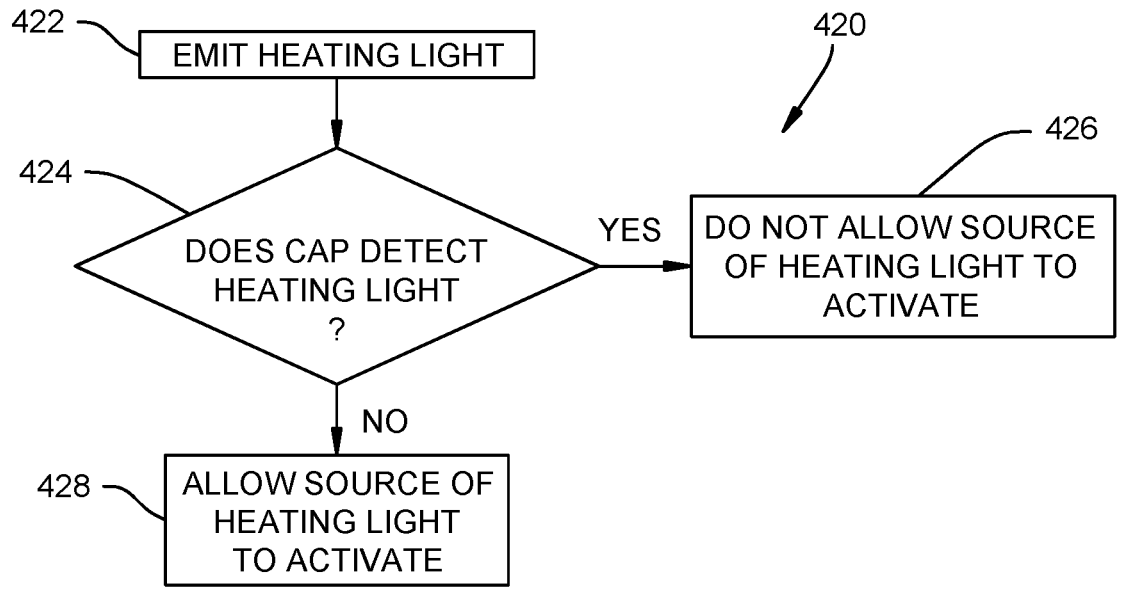

A third method 420 (FIG. 9C) for determining if the endoscope 22 includes the distal window 99 is to use the temperature sensitive cap 110 described above to verify that the endoscope 22 includes the distal window 99 by confirming (or not confirming as the case may be) the absence of heating light being emitted from the endoscope 22 when the temperature sensitive cap 110 is placed on an end of the endoscope 22. The third method 420 includes emitting heating light from the endoscope 22 at step 422. If the heating light (or a threshold amount of the heating light if the distal window 99 is not 100% absorptive of the heating light) is detected by the cap 110 at step 424, the temperature sensitive cap 110 can send a signal instructing the light source console 28 to turn off the source 104 of heating light because the endoscope 22 does not have the distal window 99 at step 426. If the heating light is not detected at step 424, the temperature sensitive cap 110 can send a signal to the light source console 28 instructing the light source console 28 to use the source 104 of heating light because the endoscope 22 does have the distal window 99 at step 428.

In the illustrated example, it is contemplated that the temperature sensitive cap 110 can communicate with the light source using any of the methods described above for communicating information from the temperature sensitive cap 110 to the light source console 28. The heating light and the imaging light can be distinguished by the temperature sensitive cap 110 using a frequency-limited sensor that senses the heating light, using filter optics that allow the heating light which passes thereby to be sensed by a sensor or by having the light source console 28 sequentially modulate the imaging light and the heating light in order to allow the temperature sensitive cap 110 to detect the imaging light and detect the absence of the heating light (if the endoscope 22 includes the distal window 99).

Figure 11:
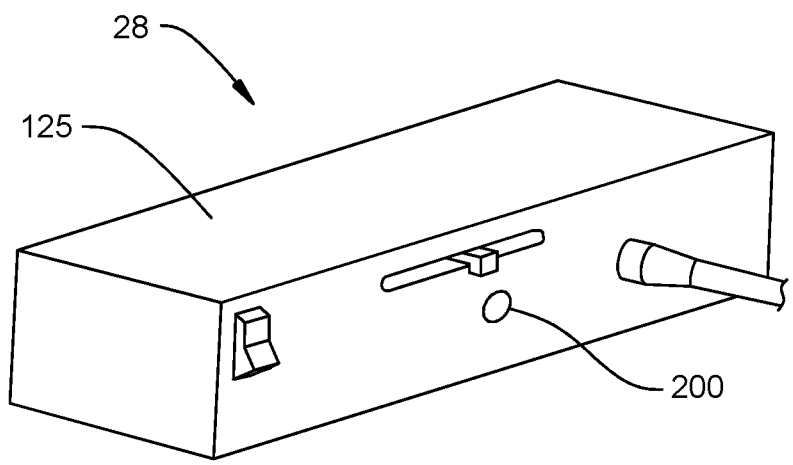
FIG. 11 is a perspective view of a console or light source of the endoscopic system having a sensor thereon.
Figure 9D:
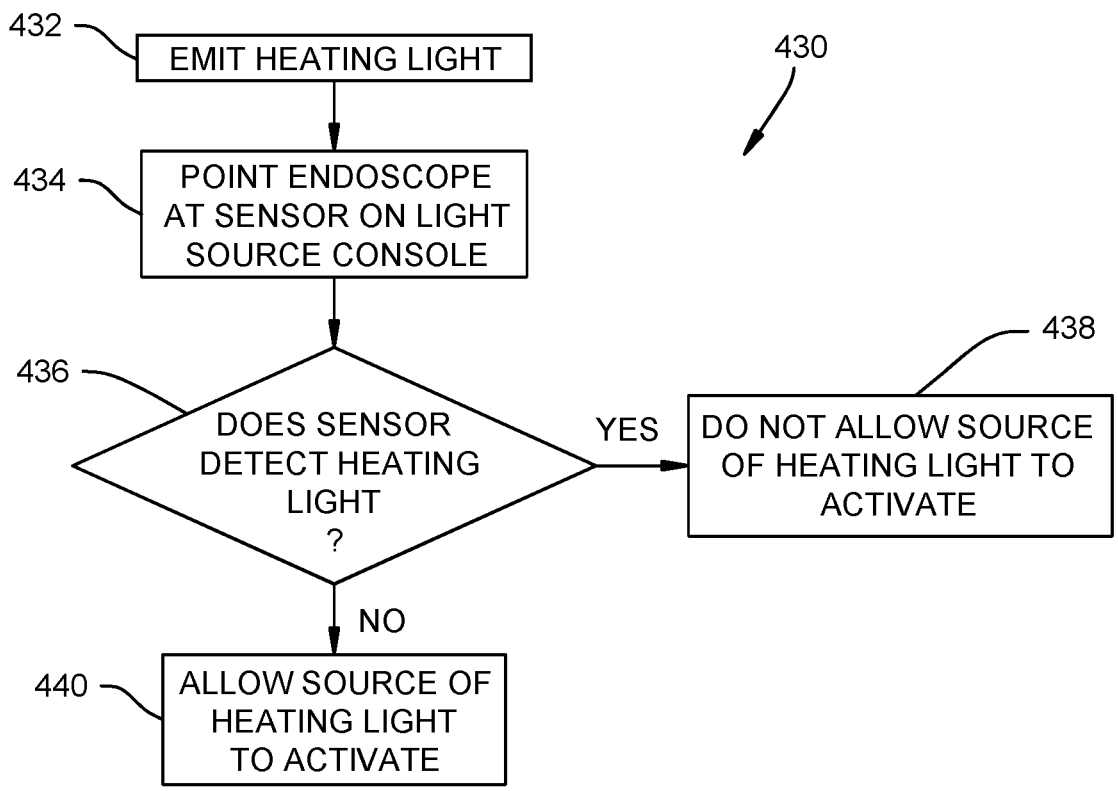

A fourth method 430 (FIG. 9D) for determining if the endoscope 22 includes the distal window 99 is to add a sensor 200 to the housing 125 of the light source console 28 as shown in FIG. 11, emit heating light at step 432 and point the endoscope 22 at the sensor 200 at step 434 to verify that the endoscope 22 includes the distal window 99 by confirming (or not confirming as the case may be) the absence of heating light being emitted from the endoscope 22 at step 436. If the heating light is detected at step 436, the light source console 28 turns off the source 104 of heating light because the endoscope 22 does not have the distal window 99 at step 438. If the heating light is not detected at step 436, the light source console 28 will use the source 104 of heating light because the endoscope 22 does have the distal window 99 at step 440.

In the illustrated embodiment, the heating light and the imaging light can be distinguished by the sensor 200 using a frequency-limited sensor that senses the heating light, using filter optics that allow the heating light which passes thereby to be sensed by a sensor or by having the light source console 28 sequentially modulate the imaging light and the heating light in order to allow the sensor 200 to detect the imaging light and detect the absence of the heating light (if the endoscope 22 includes the distal window 99).

Communicating Endoscope

Figure 12:
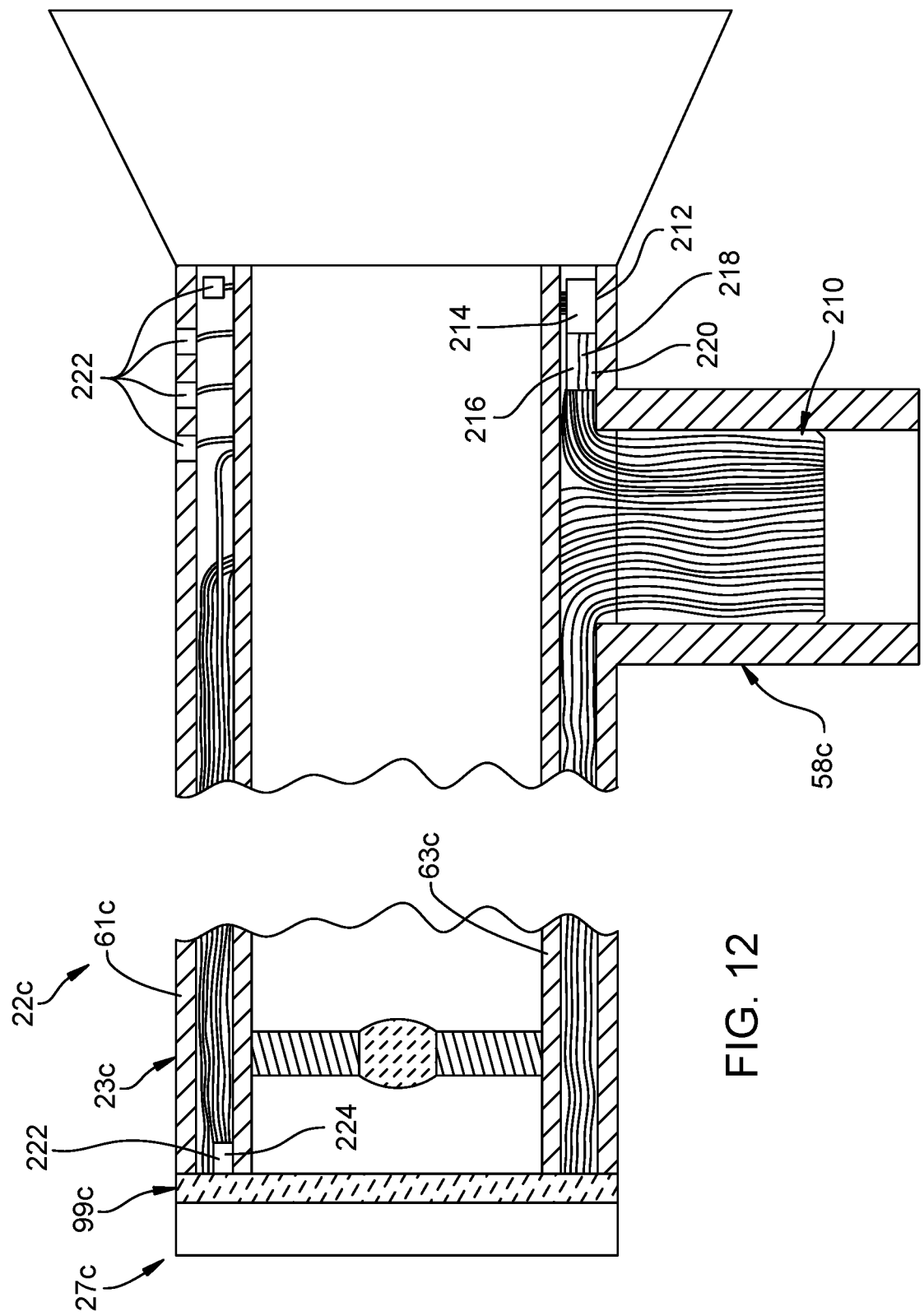
FIG. 12 is a schematic view of a first embodiment of a communicating endoscope of the present invention.

FIG. 12 illustrates another embodiment of the endoscope system including a communicating endoscope 22c. Since communicating endoscope 22c is similar to the previously described endoscope 22, similar parts appearing in FIGS. 1-3A and FIG. 12, respectively, are represented by the same reference number, except for the suffix "c" in the numerals of the latter. The communicating endoscope 22c includes the shaft 23c and the light port 58c. A plurality of optic fibers 210 run from the light port 58c to provide the heating light to the distal window 99c to heat the distal window 99c along with providing imaging light to the distal end 27c of the endoscope 22c as described above. The plurality of optic fibers 210 extend between the tubular outer housing 61c and the inner tubular housing 63c of the shaft 23c. Some of the optic fibers 210 also run from the light port 58c to a control and communication system 212 within the endoscope 22c. The communicating endoscope 22c is configured to be connected to the light source console 28 having the source of imaging light 102, the source of heating light 104, the mirror 106, and the detector 152 as described in FIG. 6 above. It is contemplated that light pipe(s) could be employed instead of optic fibers 210.

In the illustrated example, the control and communication system 212 in the communicating endoscope 22c receives power from the light source console 28 and communicates information to the light source console 28. The control and communication system 212 comprises an integrated circuit having a microcontroller 214, a photo cell 216, an electromagnetic light emitter 218 and a detector 220. The microcontroller 214, the electromagnetic light emitter 218 and the detector 220 are all powered by the photo cell 216. The illustrated photo cell 216 is connected to a plurality of the optic fibers 210 and receives heating light and imaging light from the light source console 28. In the illustrated example, the heating light and the imaging light are multiplexed in the output of the light source console 28 and/or the transmission cable 46 without the heating light and the imaging light being separated when entering or within the communicating endoscope 22c. Therefore, the photo cell 216 will receive heating light and/or imaging light during use. However, as discussed in more detail below, the heating light, the imaging light and/or a third wavelength of light can be separated when entering the communicating endoscope 22c or within the communicating endoscope 22c such that only a selected wavelength of light reaches the photo cell 216 from the light source console 28. The light reaching the photo cell 216 causes the photo cell 216 to power the components of the communicating endoscope 22c that require power or stores the power in the control and communication system 212 for later use. The photo cell 216 allows for efficient energy storage collection, thereby allowing the energy to be transformed to usable levels and stored for future high power demand processes and also provides a means for allowing the electromagnetic light emitter 218 to communicate with the light source console 28 as discussed below (including communicating the status of the stored charge in the control and communication system 212).

The illustrated control and communication system 212 communicates information to and from the light source console 28 in order to efficiently operate the communicating endoscope 22c. The control and communication system 212 can include the electromagnetic light emitter 218 connected to at least one optic fiber 210 for communicating with the light source console 28. The electromagnetic light emitter 218 can emit any wavelength of light under control of the microcontroller 214 to send a signal or signals to the light source console 28. It is contemplated that the electromagnetic light emitter 218 can be at least one LED. The detector 220 receives the heating light, the imaging light and/or a third wavelength of light to communicate to the control and communication system 212 that the light source console 28 is capable of receiving and using the data sent by the electromagnetic light emitter 218. If the detector 220 does not receive information that the light source console 28 is capable of receiving and using the data sent by the electromagnetic light emitter 218, the control and communication system 212 will turn off the electromagnetic light emitter 218 or otherwise prevent the electromagnetic light emitter 218 from sending data. The detector 220 can be any detector capable of detecting a certain wavelength of light. For example, the detector 220 can be an infrared photodiode. It is contemplated that the communicating endoscope 22c could be used without the electromagnetic light emitter 218.

In the illustrated example, a plurality of sensors 222 can be functionally connected to the microcontroller 214 for sensing properties of the communicating endoscope 22c. For example, the communicating endoscope 22c can include a temperature sensor 224 adjacent the distal window 99c for sensing a temperature of the distal window 99c. The control and communication system 212 can communicate the temperature of the distal window 99c as sensed by the temperature sensor 224 to turn on or off the source 104 of heating light as needed to maintain the distal window 99c at a desired temperature. The sensors 222 can also include an exterior temperature sensor, at least one accelerometer, a humidity sensor, an air/gas content sensor, a proximity sensor, an exterior pressure sensor, a force sensor and/or a sensor for detecting waves (e.g., radio frequency waves, infrared light, visual light, ultraviolet light and/or magnetic waves).

The illustrated sensors 222 can be used to communicate properties of the communicating endoscope 22c to the light source console 28. For example, the at least one accelerometer and/or the force sensor can sense if the communicating endoscope 22c has had a dramatic change in acceleration such when the communicating endoscope 22c is dropped or otherwise violently moved to communicate that the communicating endoscope 22c may be broken. Additionally, the exterior pressure sensor, the humidity sensor, the air/gas content sensor, and/or the exterior pressure sensor can be used along with an internal timer within the microcontroller 214 to determine if the communicating endoscope 22c has been cleaned (e.g., through autoclaving) and/or cleaned for a predetermined period of time. If the communicating endoscope 22c has not been sufficiently cleaned, the communicating endoscope 22c can communicate with the light source console 28 to notify a user of the endoscope system that the particular communicating endoscope 22c should not be used without further cleaning. The sensors 222 can also be used to determine if other cleaning methods (e.g., exposure to ultraviolet light) have been used and communicate the sufficiency of cleaning using this method to the light source console 28. Additionally, one of the sensors 222 could be used to measure the temperature of the shaft 23c of the communicating endoscope 22c and communicate the same to the light source console 28 to allow the light source console 28 to turn off if the shaft 23c is too hot (e.g., because of, for example, the communicating endoscope 22c being used in an improper environment such as when the communicating endoscope 22c is intended for use in a fluid-filled joint is then improperly used in an ENT procedure where there is no fluid present to help keep the communicating endoscope 22c cool). A temperature sensing sensor 222 could also be used to shut off the power of temperature sensitive components of the control and communication system 212 if the exterior temperature raises above a certain temperature. Moreover, the communicating endoscope 22c could be configured to send periodic transmissions to the light source console 28 (e.g., signals representing that the status of the communicating endoscope 22c is functioning properly) so that hazardous conditions such as accidental disconnection of the transmission cable 45 from the communicating endoscope 22c could be detected from the loss of the periodic transmissions and the source 102 of imaging light could be turned off to prevent the high-intensity imaging light from escaping a disconnected end of the transmission cable 48 to prevent injuries (e.g., eyesight damage and/or burning).

The illustrated communicating endoscope 22c could also communicate other information not sensed by the sensors 222 to the light source console 28. For example, the communicating endoscope 22c could communicate the type of endoscope as saved in memory in the microcontroller 214 (for example, to allow the light source console 28 to configure itself to maximized compatibility of the communicating endoscope 22c with the light source console 28), a lifetime of the communicating endoscope 22c (calculated, for example, using a clock in the CPU or by including information when the communicating endoscope 22c was manufactured), service hours of the communicating endoscope 22c (measured, for example, by the total time that the detector 220 has received light), and operational information of the particular communicating endoscope 22c. Another example of information communicated from the communicating endoscope 22c to the light source console 28 can be the capability of the communicating endoscope 22c to use advanced imagining techniques (for example, capability of reading infrared wavelengths given off by indocyanine green dye in a patient).

FIG. 13 illustrates a second embodiment of the communicating endoscope 22d. Since the second embodiment of the communicating endoscope 22d is similar to the previously described first embodiment of the communicating endoscope 22c, similar parts appearing in FIG. 12 and FIG. 13, respectively, are represented by the same reference number, except for the suffix "d" in the numerals of the latter. The second embodiment of the communicating endoscope 22d is substantially identical to the first embodiment communicating endoscope 22c, except that the fiber optics 210d do not connect to the cell 216d (although the fiber optics still do connect to the electromagnetic light emitter 218d and the detector 220d). Instead of light powering the cell 216d, the cell 216d can be powered by another source. For example, the cell 216d can be powered by thermal energy, vibrations, radio frequency waves or inductive transducers using methods well known to those skilled in the art.

If an inductive transducer is used, the cell 216d can be supplied with power by an inductive coupler on the camera or could be a long-range resonant magnetic coupler positioned near the endoscope when same is not in use.

Figure 14:
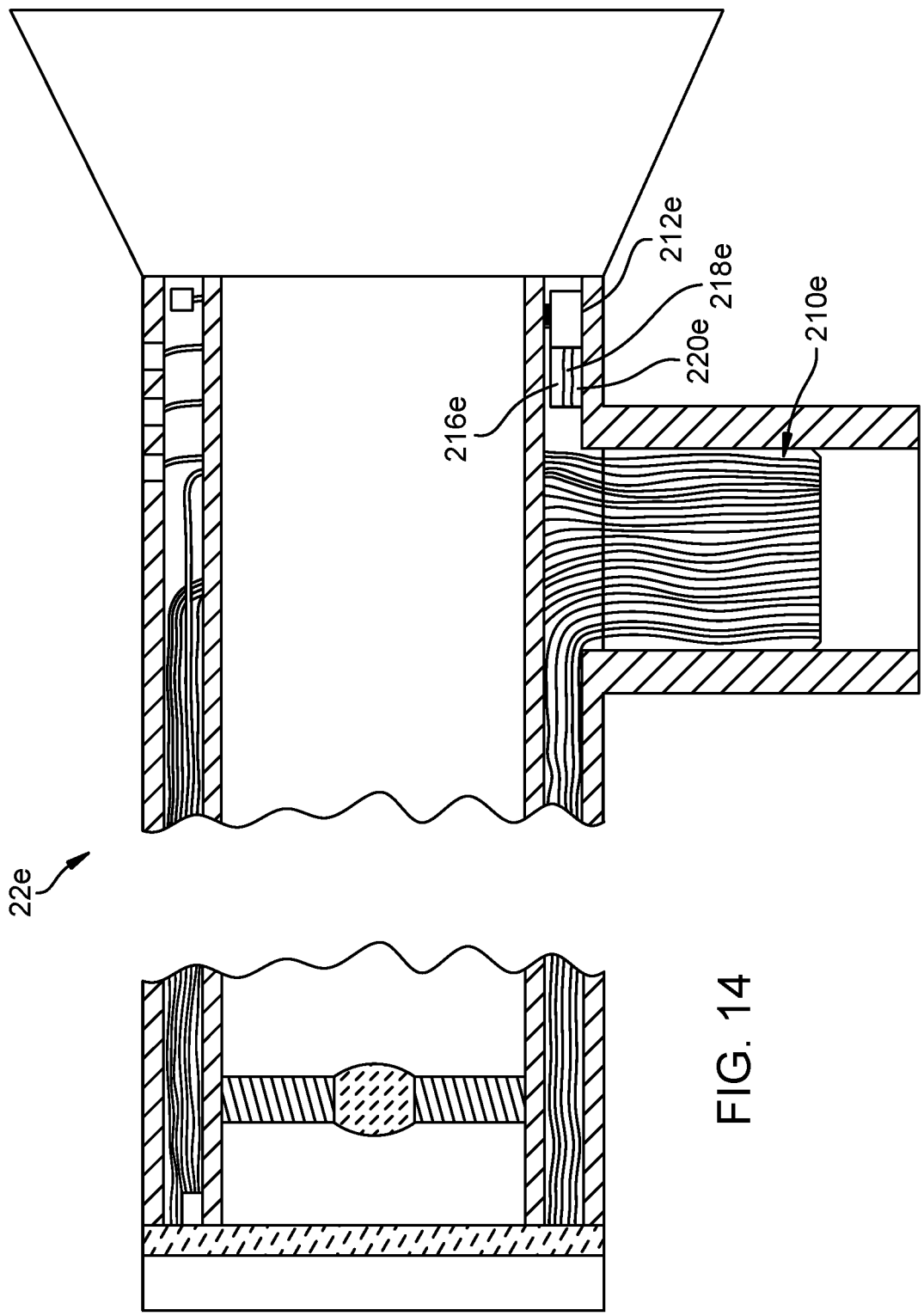
FIG. 14 is a schematic view of a third embodiment of a communicating endoscope of the present invention.

FIG. 14 illustrates a third embodiment of the communicating endoscope 22e. Since the third embodiment of the communicating endoscope 22e is similar to the previously described second embodiment of the communicating endoscope 22d, similar parts appearing in FIG. 13 and FIG. 14, respectively, are represented by the same reference number, except for the suffix "e" in the numerals of the latter. The third embodiment of the communicating endoscope 22e is substantially identical to the second embodiment communicating endoscope 22d with the fiber optics 210e not connected to the cell 216e, except that the fiber optics 210e also do not connect to the electromagnetic light emitter and the detector. Instead of communicating the light source console 28 with the fiber optics 210e and the transmission cable 46, the electromagnetic light emitter 218d is replaced with a wireless sending device 218e and the detector 220d is replaced with a wireless receiving device 220e (or the wireless sending device 218e and the wireless receiving device 220e can be combined into a single unit). For example, the wireless sending device 218e and the wireless receiving device 220e can communicate using a low power wireless or WPAN configuration, employing a wireless communication protocol that has a limited communication distance (e.g., Zigbee, Bluetooth, SimpliciTI and ANT).

Figure 15:
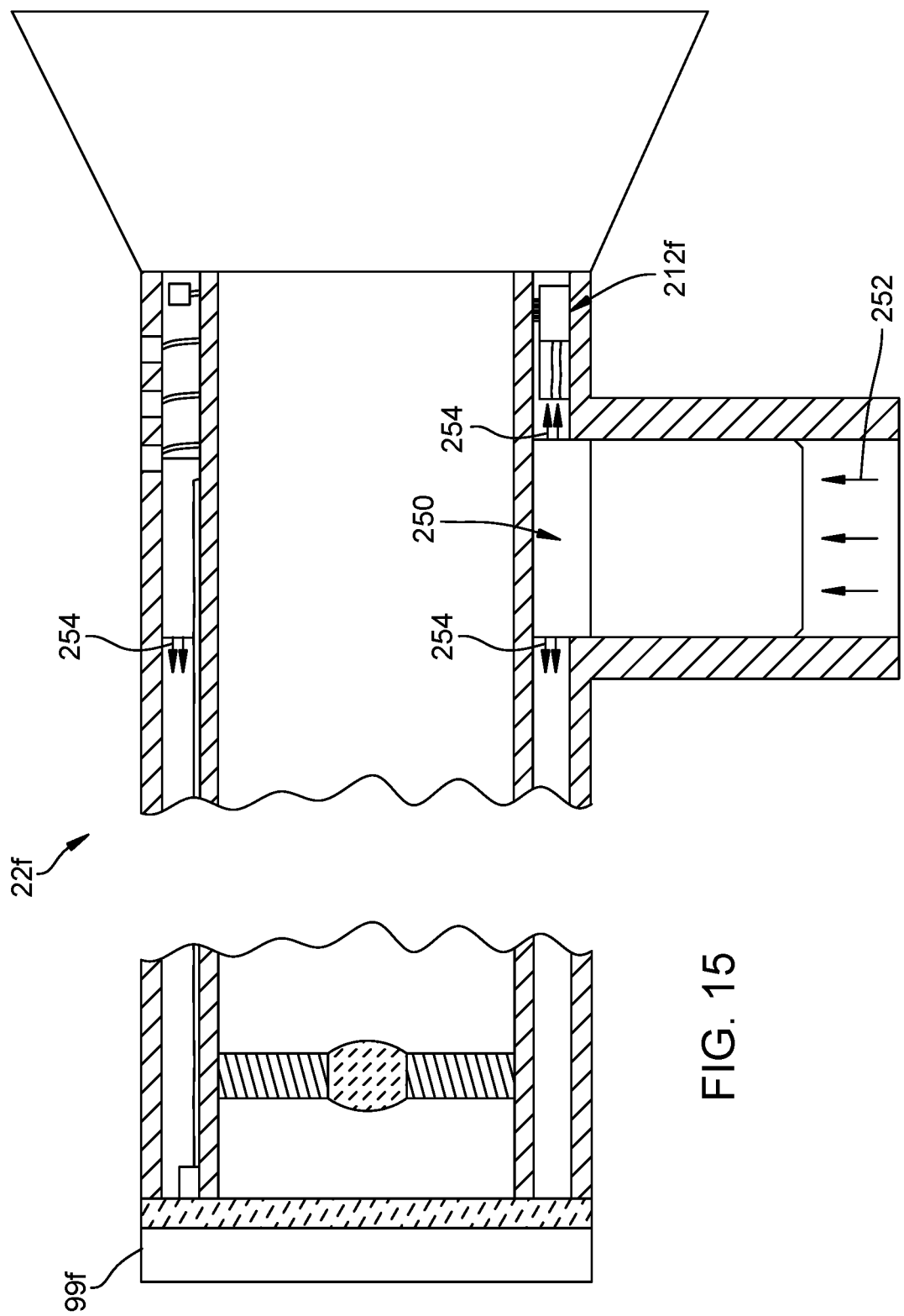
FIG. 15 is a schematic view of a fourth embodiment of a communicating endoscope of the present invention.

FIG. 15 illustrates a fourth embodiment of the communicating endoscope 22f. Since the fourth embodiment of the communicating endoscope 22f is similar to the previously described first embodiment of the communicating endoscope 22c, similar parts appearing in FIG. 12 and FIG. 15, respectively, are represented by the same reference number, except for the suffix "f" in the numerals of the latter. The fourth embodiment of the communicating endoscope 22f is substantially identical to the first embodiment communicating endoscope 22c, except that the fiber optics 210 are replaced with a light splitting and/or combining device 250. The light splitting and/or combining device 250 will redirect electromagnetic waves 252 coming from the light source console 28 and the transmission cable 46 and redirect the redirected electromagnetic waves 254 toward the distal window 99f and the control and communication system 212f. It is contemplated that the light splitting and/or combining device 250 could be a prism or prisms, a dichroic splitter/combiner, a fractional splitter/combiner (e.g., a half silvered mirror), or a wavelength-division-multiplexing module). It is contemplated that the light splitting and/or combining device 250 could redirect a certain band or certain bands of wavelength of light toward the distal window 99f (e.g., the heating light and the imaging light) while redirecting a third band of wavelength of light or allowing the third band of wavelength of light to pass therethrough (e.g., light going to and/or from the control and communication system 212f). It is also contemplated that free space coupling could be used.

In all of the communicating endoscopes 22c-22f described above, all of the features could be used with any of the communicating endoscopes 22c-22f. For example, the communicating endoscopes 22c-22f could be used with a distal window 99 that heats to prevent fogging. Furthermore, the communicating endoscopes 22c-22f could be used with a cell 216 that receives power from light or from other means as described above, or all of the communicating endoscopes 22c-22f could be used with the electromagnetic light emitter 218 and/or the detector 220 (i.e., one or both thereof) that communicate using light through the transmission cable 46 or through any wireless methods as described above. Finally, any of the communicating endoscopes 22c-22f could be used with or without the sensors 222 described above.

Although the present invention has been described with reference to specific exemplary embodiments, it will be recognized that the invention is not limited to the embodiments described, but can be practiced with modification and alteration within the spirit and scope of the appended claims. Accordingly, the specification and drawings are to be regarded in an illustrative sense rather than a restrictive sense. For example, the foregoing has involved surgical procedures specific to humans. It will be appreciated that the systems and methods described herein may also be applied to veterinary applications and non-biological applications, for example for inspection of fluid chambers in industrial plants and transport devices. Moreover, it is contemplated that any of the approaches for selecting or setting the power level of the heating light can be used in conjunction with any of the methods for determining if the endoscope 22 includes the distal window 99. Moreover, it is contemplated that the distal window 99 of the present invention could be used on an endoscope having chip on tip technology wherein the chip emits light (e.g., an LED), with the chip emitting a broad spectrum of light including both the imaging light and the heating light, a plurality of chips emitting imaging light and heating light, and/or a combination of at least one chip and light coming from the light source console 28.

Although particular preferred embodiments of the invention have been disclosed in detail for illustrative purposes, it will be recognized that variations or modifications of the disclosed apparatus, including the rearrangement of parts, lie within the scope of the present invention.

Communicating Endoscopic Information

Figure 16:
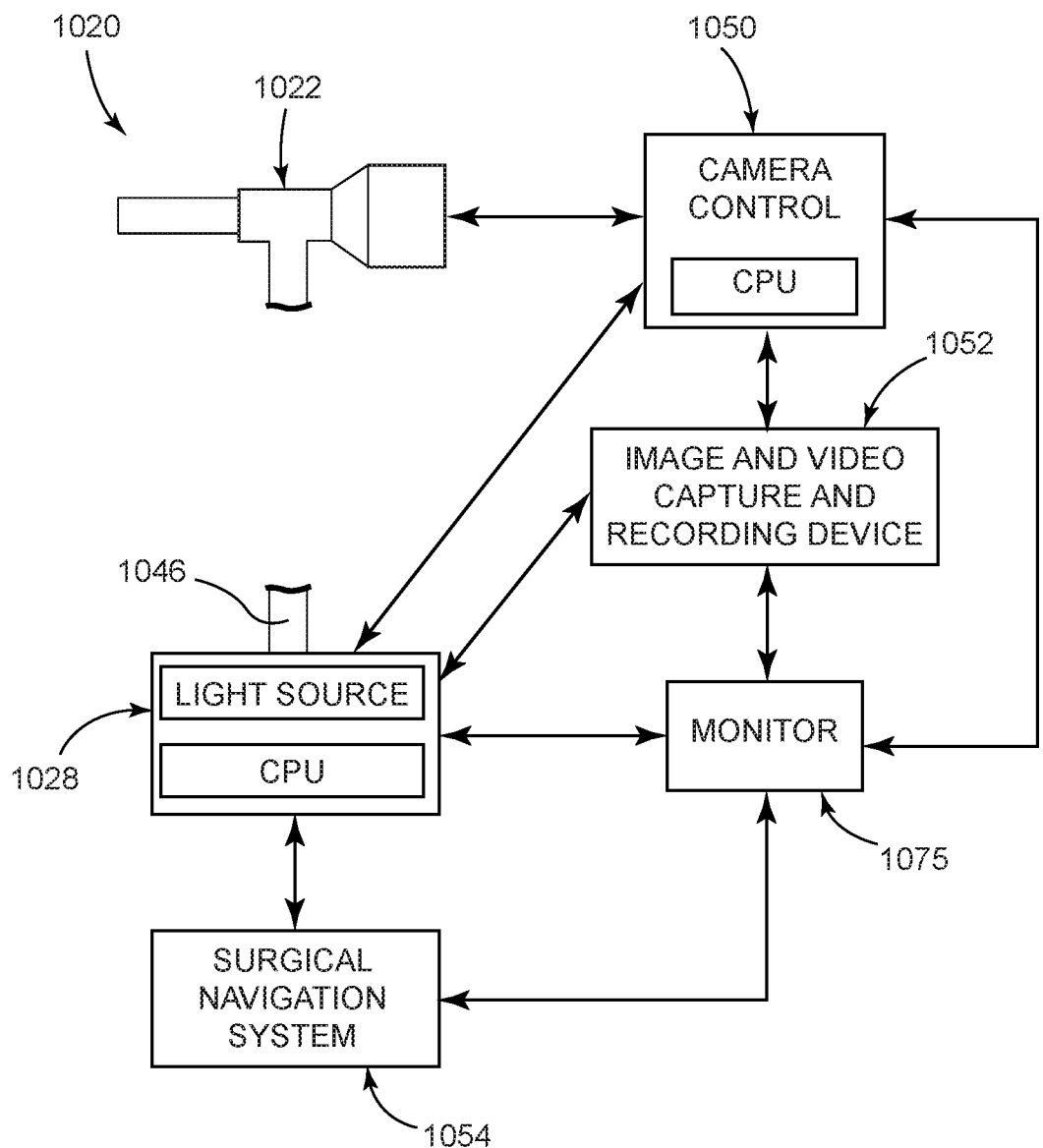
FIG. 16 is a schematic view of an endoscopic system including various components that can be adjusted using the information from a communicating endoscope of the present invention.

FIGS. 12-15 illustrate embodiments of communicating endoscopes 22c-f. As outlined above, the communicating endoscopes 22c-f can transmit information about the communicating endoscopes 22c-f to the light source console 28 for improving and altering the image captured by the camera 73 taken through the communicating endoscopes 22c-f. FIG. 16 illustrates an endoscopic system 1020 including various components that can be adjusted using the information from the communicating endoscopes 22c-f (renumbered as 1022 in FIG. 16) transmitted to the light source console 1028 via the transmission cable 1046. As illustrated in FIG. 16, the endoscopic system 1020 includes the communicating endoscope 1022, the transmission cable 1046, the light source console 1028, a camera control 1050, an image and video capture and recording device 1052, a surgical navigation system 1054 and the monitor 1075. It is contemplated that the image and video capture and recording device 1052 and/or the surgical navigation system 1054 can include a dedicated monitor (either integrated (e.g., as a touchscreen) or separate).

In the illustrated example, the surgical navigation system 1054 allows for positions of special instruments to be tracked as shown on images of the patient as the surgeon moves the instruments, thereby allowing the surgeon to navigate a location of the instrument within the patient. An example of a surgical navigation system is disclosed in U.S. Pat. No. 8,657,809 entitled SURGICAL NAVIGATION SYSTEM, the entire contents of which are incorporated herein by reference.

The illustrated image and video capture and recording device 1052 is capable of displaying and recording images and videos. The image and video capture and recording device 1052 can include an internal hard drive for storing captured images and videos and can also communicate with a picture archiving and communication system (PACS), as is well known to those skilled in the art, to save images and video in the PACS and for retrieving images and videos from the PACS. The image and video capture and recording device 1052 can also display any saved images (e.g., from the internal hard drive or from the PACS) on the touchscreen monitor and/or the additional monitor. It is contemplated that the image and video capture and recording device 1052 could obtain or create images of a patient during a surgical procedure from a variety of sources (e.g., from video cameras, video cassette recorders, X-ray scanners (which convert X-ray films to digital files), digital X-ray acquisition apparatus, fluoroscopes, CT scanners, MRI scanners, ultrasound scanners, CCD devices, and other types of scanners (handheld or otherwise)). An example of an image and video capture and recording device 1052 is the SDC3 HD Information Management System (with device control) as sold by Stryker Corporation of Kalamazoo, Mich.

In the illustrated example, the information obtained from the communicating endoscope 1022 and can be used to improve or alter the output of the light source console 1028, the camera control 1050, the image and video capture and recording device 1052, the surgical navigation system 1054 and the monitor 1075 or any other device communicating with the light source console 1028. Accordingly, the communicating endoscope 1022 communicates with the light source console 1028, which can in turn communicate with the camera control 1050, the image and video capture and recording device 1052, the surgical navigation system 1054, the monitor 1075 and/or any other device communicating with the light source console 1028.

Figure 17:
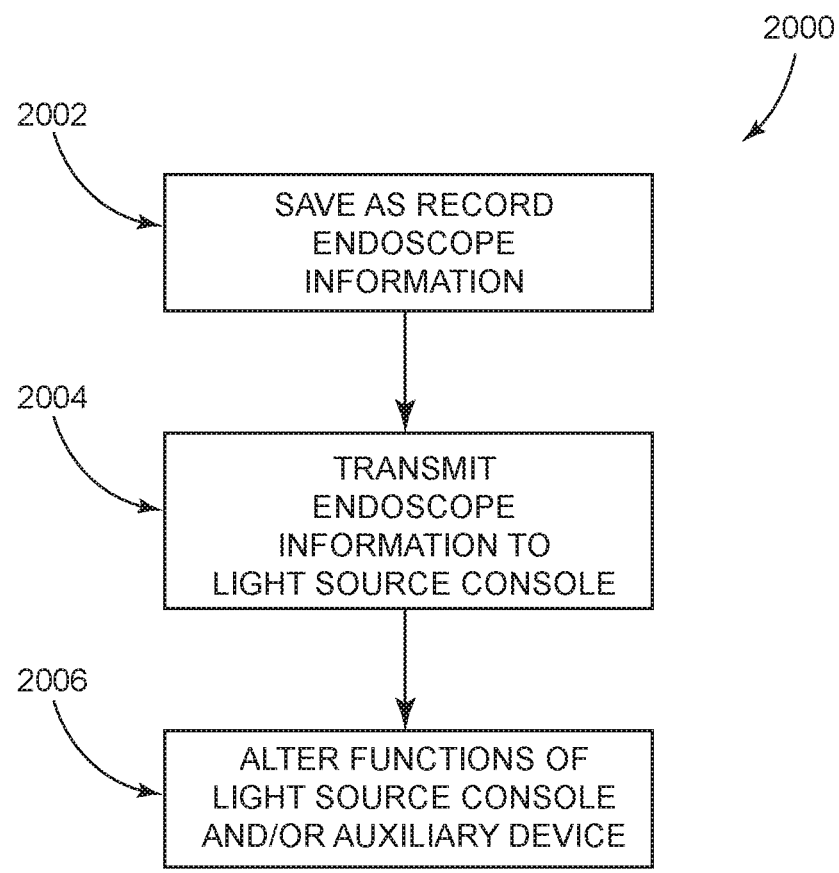
FIG. 17 is a schematic view of a method of altering functions of an operative device with information obtained from a communicating endoscope of the present invention.

FIG. 17 illustrates a method 2000 of altering functions of at least one of the light source console 1028 and an auxiliary device (e.g., the camera control 1050, the image and video capture and recording device 1052, the surgical navigation system 1054 and/or the monitor 1075) with information obtained from the communicating endoscope 1022. The method 2000 includes saving or recording information related to the endoscope 1022 in the endoscope 1022 at step 2002. The information related to the endoscope can be saved or recorded in the endoscope 1022 in any manner. For example, the information related to the endoscope can be saved or recorded in the control and communication systems 212, 212, 212d, 212e or 212f described above. The information related to the endoscope can also be saved in an RFID chip 3000 (see FIG. 18) or other memory element located in the endoscope 1022, with an example of such RFID chip 3000 discussed below.

The next step in the method 2000 is to transmit the information related to the endoscope to the light source console 1028 at step 2004. In the illustrated example, the information related to the endoscope is transmitted to the light source console 1028 via the transmission cable 1046. However, it is contemplated that the information related to the endoscope can be transmitted wirelessly directly from the endoscope 1022 to the light source console 1028. The final step in the method 2000 is to alter functions of at least one of the light source console 1028 and an auxiliary device dependent upon the information related to the endoscope at step 2006. The auxiliary devices that are altered because of the information related to the endoscope receive the information related to the endoscope from the light source console 1028 (either directly or indirectly). If the device being altered includes the auxiliary device (either individually, with other auxiliary devices and/or with the light source console 1028), step 2006 includes transmitting the information related to the endoscope from the light source console 1028 to the auxiliary device.

In the illustrated example, the information related to the endoscope can be any information related the endoscope itself. For example, the information related to the endoscope can include any of the following: type of endoscope specialty, information related to manufacturing and assembly of the endoscope, service hours of the endoscope, operational information of the endoscope, capability of using advanced imaging techniques with the endoscope, physical differentiating parameters of the endoscope, and/or optical parameters of the endoscope. The above list is not exhaustive and is for illustrative purposes only. The information related to the endoscope can be used to alter the light source console 1028 and/or devices connected thereto or communicating therewith (i.e., the auxiliary devices). It is contemplated that a lack of information as to capabilities of the endoscope 1022 could be the information related to the endoscope that alters the light source console 1028 and/or devices connected thereto or communicating therewith.

If the information related to the endoscope is a type of endoscope specialty, the type can be arthroscopy, laparoscopy, cystoscopy, hysteroscopy, ENT or neurosurgery. The above list is not exhaustive and is for illustrative purposes only. Such information can be used to alter the light source console 1028. For example, the light source console 1028 can be altered to increase voltage to an LED or other light source in the light source console 1028 to account for the endoscope's decreased ability to transmit a certain color (e.g., green light for use in urology) or otherwise configuring the light to maximize capabilities of images obtained through the endoscope. The type of endoscope specialty can also be used to alter the surgical navigation system 1054. For example, the surgical navigation system 1054 can be used to locate and highlight critical structures with respect to a tracked instrument based on the type of endoscope specialty. The type of endoscope specialty can also be used to alter the monitor 1075. For example, the settings of the monitor 1075 can be altered depending on the type of endoscope specialty. The type of endoscope specialty can also be used to alter the camera control 1050. For example, the camera control 1050 typically has settings depending on the type of endoscope specialty and the camera control 1050 can be automatically changed to the particular type of endoscope specialty upon connection of the endoscope 1022 to the light source console 1028 via the transmission cable 1046. The type of endoscope specialty can also be used to alter the image and video capture and recording device 1052. For example, the image and video capture and recording device 1052 could use the type of endoscope specialty to configure itself (e.g., for showing images or overlays on a touchscreen or a connected monitor 1075 or for case management) or devices connected thereto and communicating therewith (e.g., a combined radio frequency ablation and shaving device). The above examples of devices that can be altered depending on the type of endoscope specialty and how those devices are altered is not exhaustive and is for illustrative purposes only.

In the illustrated example, the information related to manufacturing and assembly of the endoscope can be used to alter devices communicating with the light source console 1028. For example, the information related to manufacturing and assembly of the endoscope can include a lifetime of the endoscope 1022, a date of manufacture of the endoscope 1022, a part number of the endoscope 1022, a serial number of the endoscope 1022, capability to use near-infrared visualization and/or an age of the endoscope 1022. The above list is not exhaustive and is for illustrative purposes only. The information related to the manufacturing and assembly of the endoscope can be used to alter the light source console 1028 and devices connected thereto or communicating therewith (i.e., the auxiliary devices). For example, the light source console 1028 can be adjusted to not emit near-infrared light if the endoscope 1022 is not compatible for this format. In such a situation, the information related to the manufacturing and assembly of the endoscope would be an absence of information that the endoscope 1022 is compatible with near-infrared light. As another example, the camera control 1050 can be adjusted to modify an image captured by the camera to account for optical performance degradation because of the age of the endoscope 1022.

Further examples of information related to the endoscope 1022 and the devices affected thereby include: recording service hours or sterilization cycles of the endoscope 1022 to then be saved in a centralized instrument tracking system as communicated to such system by the light source console 1028 and can be used to retire the endoscope 1022 and/or order a new endoscope; operational information of the endoscope 1022 can include whether the endoscope 1022 includes systems that are active and functional, are passive and/or if a failure has occurred (e.g., the endoscope is not working or removed from the transmission cable 1046); capability of using advanced imaging techniques can be used to alter the light source console 1028 to emit warming light if the endoscope 1022 can use such light as outlined in any of the embodiments above or can read specific wavelengths of light (e.g., infrared wavelengths given off by indocyanine green dye as outlined above); endoscope physical differentiating parameters including working diameter and length of the endoscope 1022 can be used by the surgical navigation system 1054 to properly visualize the endoscope 1022 and/or only allow energy to be supplied to an instrument (e.g., an RF probe) when the instrument is outside of the endoscope; and/or optical parameters of the endoscope such as field of view, direction of view, distortion at multiple locations, vignetting at multiple locations, color reproduction, optimal object distance, depth of field, optical transmission, fiber transmission/pattern, etc. can be used to alter the camera control 1050 to properly process an image thereof (e.g., removal of distortion, light rendering optimization, eliminating the white balance process by the user, automatically zooming small diameter endoscope images, increasing the dynamic range, correct for the vignetting caused by the endoscope, and improving the desaturation of images) or the surgical navigation system 1054 to locate and highlight critical structures with respect to a tracked instrument. Once again, the above list and examples are not exhaustive and are for illustrative purposes only.

Figure 18:
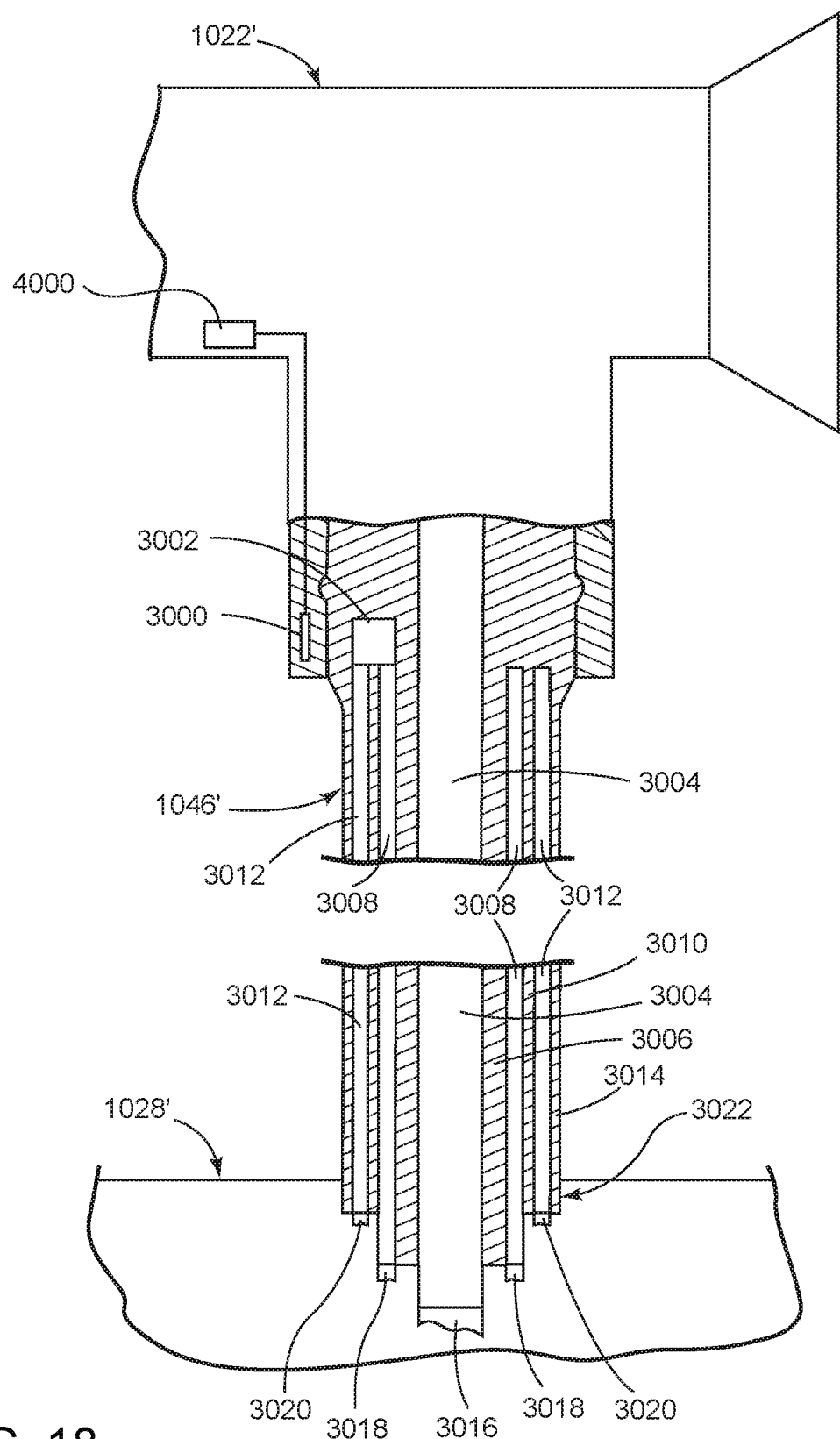
FIG. 18 is a schematic view of a fifth embodiment of a communicating endoscope of the present invention.

As outlined above, the endoscope 1022 can be any of the communicating endoscopes 22*c-f* as discussed above. The endoscope 1022 can also be the endoscope 1022' used with the light source console 1028' and the transmission cable 1046' as illustrated in FIG. 18. The endoscope 1022', the light source console 1028' and the transmission cable 1046' as illustrated in FIG. 18 can be used in the method 2000 as outlined above. The transmission cable 1046' of FIG. 18 includes a RFID reader 3002 (e.g., on a PCB) or other microcontroller that reads the information from the RFID chip 3000 in the endoscope 1022'. The illustrated transmission cable 1046' includes a center portion 3016 including a plurality of fiber optic cables for transmitting light from the light source console 1028' to the endoscope 1022', an inner cylinder 3008 for transmitting power to the RFID reader 3002 (and including a ground wire) and an outer cylinder 3012 for transmitting the information related to the endoscope from the RFID reader 3002 to the light source console 1028'. A first ring 3006 separates a center portion 3004 of the plurality of fiber optic cables from the inner cylinder 3008 and a second ring 3010 separates the inner cylinder 3008 from the outer cylinder 3012. The transmission cable 1046' can also include an outer layer 3014 protecting the interior of the transmission cable 1046'. An end of the transmission cable 1046' within the light source console 1028' has a stepped surface received within a stepped receiving hole 3022 in the light source console 1028'. A light connector 3016 within the light source console 1028' engages with the center portion 3004 to send light through the transmission cable 1046', a power connector 3018 engages with the inner cylinder 3008 to send power to the inner cylinder 3008 for the RFID reader 3002, and an information connector 3020 engages with the outer cylinder 3012 to send the information related to the endoscope to the CPU of the light source console 1028'. The RFID reader 3002 automatically reads the information on the RFID chip 3000 and sends the information related to the endoscope to the light source console 1028'. Although a particular design of a RFID reader 3002, RFID chip 3000 and transmission cable 1046' are shown, any design of the endoscope 1022', the transmission cable 1046' and the light source console 1028' could be used wherein the endoscope 1022' includes the RFID chip 3000 and the information saved thereon is sent to the light source console 1028' via the transmission cable 1046'. It is contemplated that the RFID chip 3000 could be located outside of a steel casing to limit interference, but within a polymer (e.g., PEEK) enclosure to the RFID chip 3000 (e.g., during a process of sterilizing the endoscope 1022' (e.g., autoclaving)). Likewise, the RFID reader 3002 could also be located outside of steel connection components for connecting the endoscope 1022' to the light cable 1046' to limit interference, but within a protecting polymer enclosure. It is further contemplated that the RFID reader 3002 could be located closer to the light source console 1028' or within the light source console 1028', with the RFID reader 3002 having a very long antenna that extends to a position near the RFID chip 3000 (e.g., extending to the location of the RFID reader 3002 as illustrated in FIG. 18).

In the illustrated example, it is contemplated that the RFID reader 3002 could transmit RF energy to the RFID chip 3000. The energy transmitted to the RFID chip 3000 could be used to power the RFID chip 3000 and/or other electronic components 4000 within or on the endoscope 1022 and the other electronic components 4000 could send information obtained therefrom to the RFID chip 3000 to send real time information to the RFID reader 3002 for altering functions of at least one of the light source console and an auxiliary device. For example, the other electronic components 4000 connected to the RFID chip 3000 could be a temperature sensor (e.g., a thermocouple), a pressure sensor, a gyroscope and/or an accelerometer within the endoscope 1022. The temperature sensor and the pressure sensor could obtain a temperature and pressure, respectively, and send the temperature and pressure to the RFID chip 3000, the RFID reader 3002 and to the light source console. Such information could be used to adjust the electromagnetic waves (e.g., visible light or infrared light to heat the lens of the endoscope as outlined above) emitted from the light source console (e.g., to lower the temperature of the endoscope). Such information could also be used to adjust a fluid pump (not shown) supplying liquid or removing liquid from a surgical site at the end of the endoscope. The gyroscope and/or an accelerometer could also be used to send the deflection information of the endoscope relative to a camera to the RFID chip 3000, the RFID reader 3002 and to the light source console for sending to further devices.

Although particular preferred embodiments of the invention have been disclosed in detail for illustrative purposes, it will be recognized that variations or modifications of the disclosed apparatus, including the rearrangement of parts, lie within the scope of the present invention.

What is claimed is:

1. An endoscopic system comprising:
an endoscope having saved information therein related to the endoscope;
a light source console for providing light to the endoscope; and
a light cable connected between the endoscope and the light source console, the light cable being configured to communicate the light from the light source console to the endoscope,
wherein the information related to the endoscope is relayed from the endoscope to the light source console through the light cable for altering functions of at least one of the light source console and an auxiliary device,
wherein the endoscope includes a memory element and the information related to the endoscope can be wirelessly relayed from the memory element to the light cable and the light cable includes a wireless reader for reading the information related to the endoscope from the memory element, and
wherein the wireless reader is configured to wirelessly transfer power to the memory element and the memory element is configured to transmit the power wirelessly transmitted thereto to a further electronic component within the endoscope.

2. The endoscopic system of claim 1, wherein:
the memory element comprises an RFID chip and the information related to the endoscope is wirelessly relayed from the RFID chip to the light cable.

3. The endoscopic system of claim 2, wherein:
the endoscope includes a light cable connecting portion receiving a portion of the light cable therein and the RFID chip is located in the light cable connecting portion.

4. The endoscopic system of claim 2, wherein:
the wireless reader comprises an RFID reader for reading the information related to the endoscope from the RFID chip.

5. The endoscopic system of claim 4, wherein:
the light cable includes a first connector for supplying power from the light source console to the RFID reader in the light cable and a second connector for communicating the information related to the endoscope from the RFID reader to the light source console.

6. The endoscopic system of claim 1, wherein:
the information related to the endoscope is relayed in the light cable via a wired communication system.

7. The endoscopic system of claim 6, wherein:
electromagnetic waves communicate the information related to the endoscope to the light source console via the wired communication system.

8. The endoscopic system of claim 1, wherein:
the information related to the endoscope alters an output of electromagnetic waves from the light source console.

9. The endoscopic system of claim 1, wherein:
the information related to the endoscope alters an output of the at least one auxiliary device.

10. The endoscopic system of claim 9, wherein:
the at least one auxiliary device includes at least one of a camera control, an image and video capture and recording device, a surgical navigation system and a monitor.

11. The endoscopic system of claim 1, wherein the further electronic component comprises a temperature sensor, a pressure sensor, a gyroscope, or an accelerometer.

12. The endoscopic system of claim 1, wherein at least a portion of the information related to the endoscope is generated by the further electronic component.

13. An endoscopic system comprising:
an endoscope having saved information therein related to the endoscope;
a light source console providing light to the endoscope; and
a light cable connected between the endoscope and the light source console, the light cable communicating the light from the light source console to the endoscope along with communicating the information related to the endoscope to the light source console
wherein the information related to the endoscope is wirelessly relayed from the endoscope to the light cable,
wherein functions of at least one of the light source console and an auxiliary device are altered dependent upon the information related to the endoscope,
wherein the endoscope includes a memory element and the information related to the endoscope can be wirelessly relayed from the memory element to the light cable and the light cable includes a wireless reader for reading the information related to the endoscope from the memory element, and
the wireless reader is configured to wirelessly transfer power to the memory element and the memory element is configured to transmit the power wirelessly transmitted thereto to a further electronic component within the endoscope.

14. The endoscopic system of claim 13, wherein:
the memory element comprises an RFID chip and the information related to the endoscope is wirelessly relayed from the RFID chip to the light cable.

15. The endoscopic system of claim 14, wherein:
the endoscope includes a light cable connecting portion receiving a portion of the light cable therein and the RFID chip is located in the light cable connecting portion.

16. The endoscopic system of claim 14, wherein:
the wireless reader comprises an RFID reader for reading the information related to the endoscope from the RFID chip.

17. The endoscopic system of claim 16, wherein:
the light cable includes a first connector for supplying power from the light source console to the RFID reader in the light cable and a second connector for communicating the information related to the endoscope from the RFID reader to the light source console.

18. The endoscopic system of claim 13, wherein the further electronic component comprises a temperature sensor, a pressure sensor, a gyroscope, or an accelerometer.

19. The endoscopic system of claim 13, wherein at least a portion of the information related to the endoscope is generated by the further electronic component.

20. A method of altering functions of at least one surgical device comprising:
saving information related to an endoscope within the endoscope;
connecting a light cable between the endoscope and a light source console;
providing light to the endoscope from the light source console via the light cable;
wirelessly relaying the information related to the endoscope from a memory element of the endoscope to a wireless reader of the light cable;
relaying the information related to the endoscope to the light source console through the light cable;
altering functions of the at least one surgical device dependent upon the information related to the endoscope;
wirelessly transferring power from the wireless reader to the memory element; and
transmitting the power wirelessly transmitted to the memory element to a further electronic component within the endoscope.

21. The method of claim 20, wherein:
the at least one surgical device includes the light source console.

22. The method of claim 20, wherein:
the memory element comprises an RFID chip.

23. The method of claim 22, further including:
providing the endoscope with a light cable connecting portion receiving a portion of the light cable therein; and
locating the RFID chip in the light cable connecting portion.

24. The method of claim 22,
wherein the wireless reader is an RFID reader.

25. The method of claim 24, further including:
supplying power in a first connector in the light cable from the light source console to the RFID reader; and
communicating the information related to the endoscope from the RFID reader to the light source console via a second connector in the light cable.

26. The method of claim 20, wherein:
relaying the information includes relaying the information in the light cable via a wired communication system.

27. The method of claim 26, wherein:
electromagnetic waves communicate information related to the endoscope to the light source console via the wired communication system.

28. The method of claim 20, wherein:
the at least one surgical device includes the light source console; and
altering functions of the at least one surgical device dependent upon the information related to the endoscope includes altering an output of electromagnetic waves from the light source console.

29. The method of claim 20, wherein:
the at least one surgical device includes at least one auxiliary device; and
altering functions of the at least one surgical device dependent upon the information related to the endoscope includes altering an output of the at least one auxiliary device.

30. The method of claim 29, wherein:
the at least one auxiliary device includes at least one of a camera control, an image and video capture and recording device, a surgical navigation system and a monitor.

31. The method of claim 20, wherein the further electronic component comprises a temperature sensor, a pressure sensor, a gyroscope, or an accelerometer.

32. The method of claim 20, wherein at least a portion of the information related to the endoscope is generated by the further electronic component.

* * * * *